United States Patent
Masak et al.

(10) Patent No.: US 6,956,372 B2
(45) Date of Patent: Oct. 18, 2005

(54) SYSTEM AND METHOD FOR NMR LOGGING WITH HELICAL POLARIZATION

(75) Inventors: Peter Masak, West Chester, PA (US); Sergei Knizhnik, Exton, PA (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 10/660,193

(22) Filed: Sep. 11, 2003

(65) Prior Publication Data

US 2004/0056658 A1 Mar. 25, 2004

Related U.S. Application Data

(60) Provisional application No. 60/409,773, filed on Sep. 11, 2002.

(51) Int. Cl.[7] ................................................. G01V 3/00
(52) U.S. Cl. ....................................... 324/303; 324/319
(58) Field of Search ............................... 324/307, 309, 324/303, 318, 320; 600/410; 335/296, 302, 210, 306, 209, 229, 230, 246

(56) References Cited

U.S. PATENT DOCUMENTS

| | | |
|---|---|---|
| 1,158,959 A | 11/1915 | Beach |
| 3,360,716 A | 12/1967 | Bloom et al. |
| 3,395,337 A | 7/1968 | Varian |
| 3,402,334 A | 9/1968 | Brown et al. |
| 3,617,867 A | 11/1971 | GerherdHerzog ............ 324/0.5 |
| 3,667,035 A | 5/1972 | Slichter .................... 324/0.5 R |
| 4,350,955 A | 9/1982 | Jackson et al. ............. 324/303 |
| 4,710,713 A | 12/1987 | Strikman .................... 324/303 |
| 4,717,876 A | 1/1988 | Masi et al. .................. 324/303 |
| 4,717,878 A | 1/1988 | Taicher et al. .............. 324/303 |
| 4,764,743 A * | 8/1988 | Leupold et al. ............. 335/306 |
| 4,785,245 A | 11/1988 | Lew et al. ................... 324/308 |
| 4,825,163 A | 4/1989 | Yabusaki et al. ............ 324/318 |
| 4,829,252 A | 5/1989 | Kaufman ..................... 324/309 |
| 4,875,013 A | 10/1989 | Murakami et al. ........... 324/318 |
| 4,933,638 A | 6/1990 | Kleinberg et al. ........... 324/303 |
| 4,987,368 A | 1/1991 | Vinegar ....................... 324/303 |
| 5,023,551 A | 6/1991 | Kleinberg et al. ........... 324/303 |
| 5,055,787 A | 10/1991 | Kleinberg et al. ........... 324/303 |
| 5,055,788 A | 10/1991 | Kleinberg et al. ........... 324/303 |

(Continued)

FOREIGN PATENT DOCUMENTS

| | | | |
|---|---|---|---|
| WO | WO 92/10768 | * 6/1992 | |
| WO | WO 99/08126 | 2/1999 | ........... G01R/33/44 |
| WO | WO 99/45234 | 9/1999 | ........... E21B/47/01 |

OTHER PUBLICATIONS

International Search Report in the corresponding International Application No. PCT/US03/28288.

*Primary Examiner*—Louis Arena
*Assistant Examiner*—Dxomara Vargas
(74) *Attorney, Agent, or Firm*—Jones Day

(57) ABSTRACT

Nuclear magnetic resonance well logging apparatus and method of use for geophysical examination of a borehole as the borehole is drilled. The apparatus is connected to the drill bit to follow it through the borehole as the borehole is formed. The apparatus comprises a non-magnetic protective collar with lateral protrusions or wings, which provide enhanced abrasion resistance, strength, and rigidity to the probe section. This collar is twisted about its longitudinal axis. The apparatus also comprises one or more permanent magnets within the metal collar and an antenna mounted outside of the collar. Both the magnet and the antenna are twisted about the longitudinal axis of the probe section to produce a generally helical static magnetic field and a radio frequency magnetic field that is substantially orthogonal to the static magnetic field.

29 Claims, 14 Drawing Sheets

U.S. PATENT DOCUMENTS

| | | | |
|---|---|---|---|
| 5,280,243 A * | 1/1994 | Miller | 324/303 |
| 5,291,137 A | 3/1994 | Freedman | 324/303 |
| 5,363,041 A | 11/1994 | Sezginer | 324/303 |
| 5,376,884 A | 12/1994 | Sezginer | 324/303 |
| 5,486,761 A | 1/1996 | Sezginer | 324/303 |
| 5,557,201 A | 9/1996 | Kleinberg et al. | 324/303 |
| 5,629,623 A | 5/1997 | Sezginer et al. | 324/303 |
| 5,705,927 A | 1/1998 | Sezginer et al. | 324/303 |
| 5,757,186 A | 5/1998 | Taicher et al. | 324/303 |
| 5,767,674 A | 6/1998 | Griffin et al. | 324/303 |
| 5,945,899 A * | 8/1999 | Leupold | 335/210 |
| 5,977,768 A | 11/1999 | Sezginer et al. | 324/303 |
| 6,008,646 A | 12/1999 | Griffin et al. | 324/303 |
| 6,051,973 A * | 4/2000 | Prammer | 324/303 |
| 6,173,793 B1 * | 1/2001 | Thompson et al. | 175/45 |
| 6,184,681 B1 | 2/2001 | Heidler | 324/303 |
| 6,242,913 B1 * | 6/2001 | Prammer | 324/303 |
| 6,246,236 B1 | 6/2001 | Poitzsch et al. | 324/303 |
| 6,268,726 B1 | 7/2001 | Prammer et al. | 324/303 |
| 6,429,653 B1 | 8/2002 | Kruspe et al. | 324/303 |
| 6,489,763 B1 * | 12/2002 | Goswami et al. | 324/303 |
| 6,531,868 B2 * | 3/2003 | Prammer | 324/303 |
| 6,717,404 B2 * | 4/2004 | Prammer | 324/303 |

* cited by examiner

B0 = DIRECTION OF STATIC MAGNETIC FIELD
B1 = DIRECTION OF RF INDUCED MAGNETIC FIELD

"Sensitive Volume" Shape@$\tau=3/2\pi$
$R_{sv}=6.75"$, Bsum=
(60Gauss...135Gauss)=var 30  40  50  60  70  80  90  100  110  120  130

Real Sensitive Volume Shape@$\tau=3/2\pi$
Bsum=B0=130Gauss,
$R_{sv}=(6.9"...4.8")$=var 130                                          130

SYSTEM AND METHOD FOR NMR LOGGING WITH HELICAL POLARIZATION

CROSS REFERENCE TO RELATED APPLICATIONS

This application claims benefit under 35 U.S.C. §119(e) of U.S. Provisional Application 60/409,773 filed on Sep. 11, 2002, which is incorporated by reference.

FIELD OF THE INVENTION

The present invention relates generally to nuclear magnetic resonance (NMR) measurements. More particularly, it relates to a downhole logging tool having a robust and abrasion-resistant protective collar and a conforming sensor configuration, preferably helically-shaped, for making downhole NMR signal measurements.

BACKGROUND OF THE INVENTION

The derivation of information regarding petroleum or other organic fuel deposits at an underground geological location is the subject of numerous technological approaches. The fluid flow properties of porous media have long been of interest in the oil industry. To a considerable degree this interest has been focused on nuclear magnetic resonance logging ever since A. Timur proved experimentally that NMR methods provide a rapid, non-destructive determination of porosity, movable fluid, and permeability of rock formations. See "Pulsed Nuclear Magnetic Resonance Studies of Porosity, Movable Fluid and Permeability of Sandstones," J. of Petroleum Technology, v. 21, pp. 775–86 (1969).

NMR logging is based on the observation that when an assembly of magnetic moments, such as those of hydrogen nuclei, are exposed to a static magnetic field, they tend to align along the direction of the magnetic field, resulting in bulk magnetization. The rate at which equilibrium is established in such bulk magnetization is characterized by the parameter $T_1$, known as the spin-lattice relaxation time. Another related and frequently used NMR logging parameter is the spin-spin relaxation time $T_2$ (also known as transverse relaxation time), which is an expression of the relaxation due to non-homogeneities in the local magnetic field over the sensing volume of the logging tool. Both relaxation times provide information about formation porosity, composition and quantity of formation fluid, and other parameters important in oil exploration.

Various techniques exist for disturbing the equilibrium of an assembly of nuclei in a static magnetic field in order to measure the relaxation parameters of interest. Usually, one applies a radio-frequency (RF) oscillating magnetic field in a direction substantially orthogonal to the static magnetic field. If the oscillating magnetic field has the proper resonant frequency (known in the art as the Larmor frequency, given by the expression $\omega=\gamma B_o$, where $B_o$ is the strength of the static field and $\gamma$ is the gyromagnetic ratio constant), then the spinning nuclei will be tipped away from the static magnetic field direction. The nuclei precess around the static field at the Larmor frequency and generate measurable signals until they return to equilibrium according to the $T_1$ relaxation time.

NMR measurements of parameters of a geologic formation can be done using, for example, the centralized MRIL® tool made by NUMAR, a Halliburton company, and the sidewall CMR tool made by Schlumberger. In a standard NMR measurement using these tools, the static magnetic field is provided by one or more appropriately configured magnets, and a series of RF pulses are applied to tip the spins of the nuclei in a sample volume. Signals from the precessing spins are then measured by the voltage induced in one or more receiving antennas.

In general, NMR logging devices may be separate from the drilling apparatus (in what is known as wireline logging), or they may be lowered into the borehole along with the drilling apparatus, enabling NMR measurement while drilling is taking place. The latter types of tools are known in the art as logging-while-drilling (LWD) or measurement-while-drilling (MWD) logging tools. The present invention is directed to an improvement of LWD/MWD tools.

U.S. Pat. No. 5,280,243, to Miller, discloses an NMR apparatus and method for geophysical examination of a borehole as it is being drilled. The content of the Miller patent is expressly incorporated herein for all purposes. With reference to FIGS. 1, 2, and 3 herein (corresponding to FIGS. 1, 2, and 4 of the Miller patent) the tool is made up of several sections, including drilling section 22, NMR logging section 24, and stabilizing section 26. In operation, the tool generates a gradient static magnetic field in a region adjacent to the borehole. This static field extends radially with respect to the longitudinal axis 28 of the tool (which generally coincides with the axis of the borehole) and has a generally uniform amplitude along the azimuth with respect to axis 28. A pulsed RF magnetic field is generated by the antenna 48 to excite nuclei in a substantially cylindrical shell within the borehole, which shell defines the sensitive volume extending along the length of the tool. The antenna is also used to pick up and measure signals from the sensitive volume, which are then processed to determine petrophysical properties of the material within the sensitive volume.

More specifically, the NMR logging portion of the tool 20 disclosed in the Miller patent includes a probe section having permanent magnet 46, RF antenna 48, and control section 72 made up of electronic/electrical components. The Miller patent discloses various conditions for the proper operation of the device, including the condition that the static and RF magnetic fields produced by the magnet and the antenna must remain orthogonal to each other, and thus symmetrical about the longitudinal axis 28, while the tool 20 is being rotated.

Further, the Miller patent discloses the use of a protective sleeve to protect the magnet, the antenna, and other components forming the sensor portion of the tool from the extreme conditions in the borehole. The sleeve in Miller is made of an electrically insulating material, such as fiberglass, that does not interfere with the static magnetic field or the RF electromagnetic fields. However, although fiberglass and other polymers may be fairly hard and durable under normal conditions, when placed in a borehole that is being drilled, a sleeve made of such materials is rapidly worn away by the severe mechanical abrasion and extreme temperatures. This creates a danger of damaging the delicate and expensive tool components covered by the sleeve.

Accordingly, there is a need to provide greater strength and abrasion resistance in a probe section of a wireline or MWD logging tool, while preserving the requisite orthogonality condition between the static magnetic and RF electromagnetic fields during the measurements.

SUMMARY OF THE INVENTION

In one aspect, the present invention concerns a sensor configuration for the logging section of a downhole wireline or measurement-while-drilling (MWD) logging tool. This configuration provides the high strength and abrasion resistance required to protect the sensor components of the tool, while preserving the requisite electro-magnetic conditions between the generated magnetic fields.

In accordance with a preferred embodiment of the present invention, the permanent magnet(s) and the antenna of the sensor are twisted over the span of the logging section of the tool. This twisting allows hard-surfaced wear pads to be placed on the sides of the logging section, preferably in a helical pattern, such that interference with both the static and RF magnetic fields of the tool is minimized. In this configuration there is always a point where the wear pads make contact with the borehole regardless of the rotational angle of the tool. At the same time, the requisite orthogonality condition between the static magnetic field and the RF electromagnetic field is preserved because, in a preferred embodiment, for any given cross-section the permanent magnet and associated antenna have been rotated by the same twist angle.

In a preferred embodiment, wear pads made of an abrasion resistant material are placed on the sides of the logging section of the tool. These wear pads can be made of a conductive non-magnetic material, such as metal, but will have only a minimal effect on the RF magnetic field of the tool because they do not shield the RF field from leaving the tool and penetrating into the formation. In a preferred embodiment, the wear pads are placed in a 180° helical pattern along the span of the collar, and so would always be the first part of the logging section to contact the borehole.

In a specific aspect, the present invention is directed to an NMR tool for logging while drilling. The apparatus is mounted closely adjacent the drill bit for rotational and longitudinal movement with the drill bit as it forms the bore hole. The apparatus can be operated at that time to generate the output signal indicative of properties of the materials sought to be analyzed in the region adjacent the apparatus. The probe section of the logging apparatus utilizes helical polarized static and RF magnetic fields, substantially orthogonal to each other. This allows the probe section to be constructed with lateral projections or wear pads constructed of metal or other strong and abrasion resistant material. Thus the abrasion resistance and overall strength and rigidity of the probe section can be enhanced so as to exceed that of prior art devices.

BRIEF DESCRIPTION OF THE DRAWINGS

Other objects and many attendant features of this invention will be appreciated and better understood with reference to the following detailed description when considered in connection with the accompanying drawings, wherein.

DETAILED DESCRIPTION OF THE INVENTION

Figure 1:
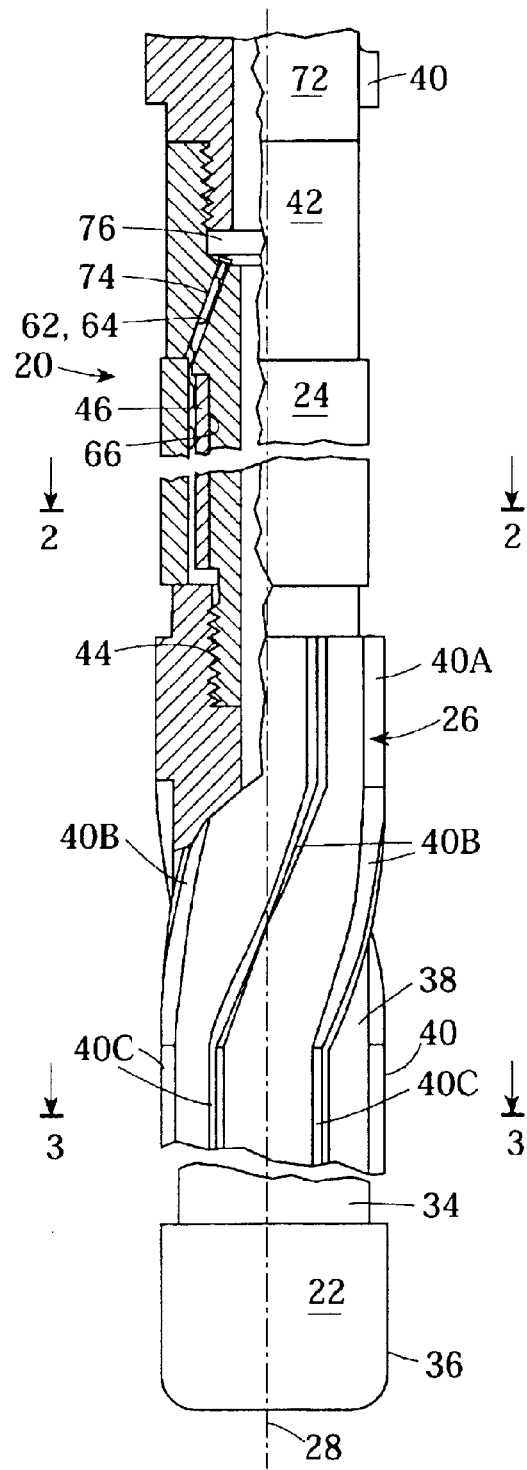
FIG. 1 is a side elevational view, partially in section, of the lower end of a prior art NMR apparatus for logging while drilling.
Figure 2:
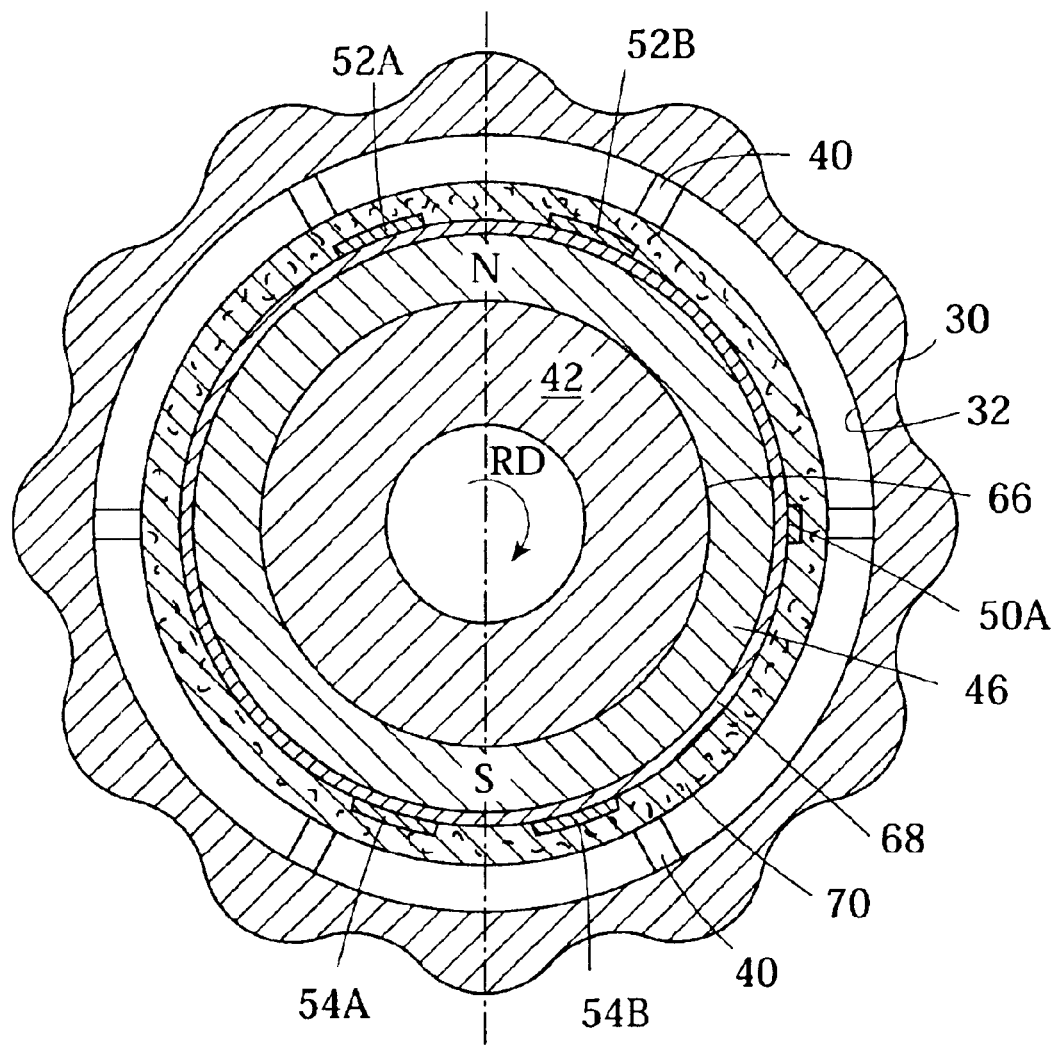
FIG. 2 is an enlarged section view of the prior art device depicted in FIG. 1, taken along line 2—2 in FIG. 1.
Figure 3:
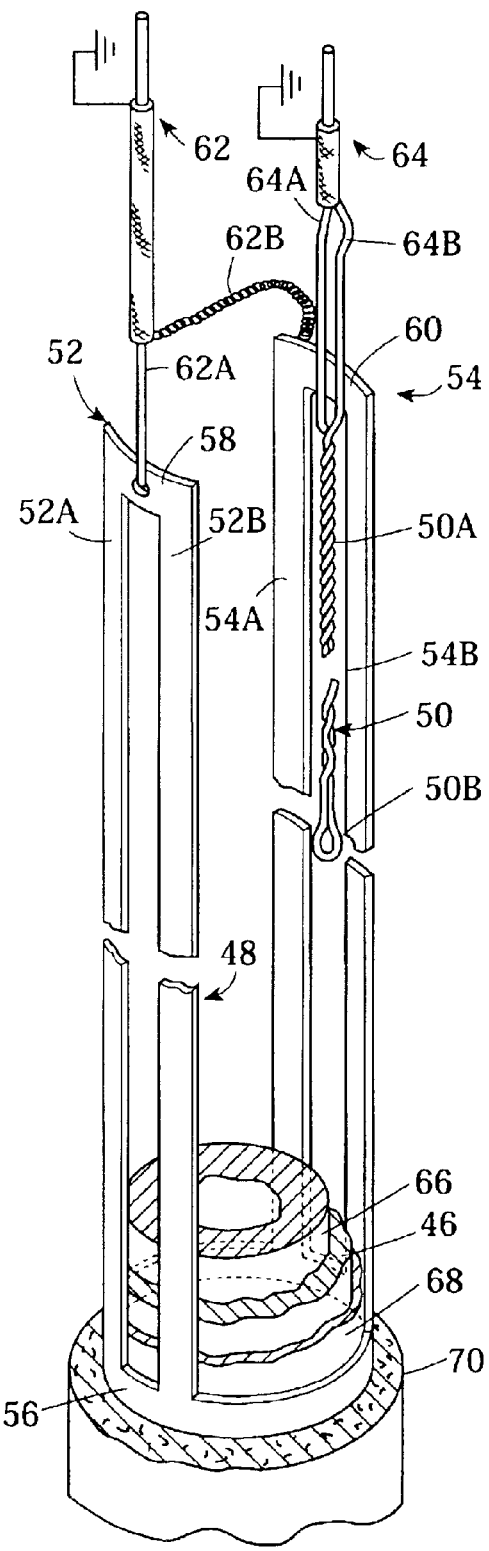
FIG. 3 is an enlarged isometric view partially in section of a portion of the prior art apparatus shown in FIG. 1.

FIGS. 1, 2, and 3 depict a prior art nuclear magnetic resonance (NMR) apparatus for logging while drilling (LWD), as disclosed in U.S. Pat. No. 5,280,243 to Miller. The content of the Miller patent is incorporated herein for all purposes. As shown in FIG. 1, the apparatus comprises drilling means 22, NMR logging means 24, and position stabilization means 26, in an integrated assembly arranged to drill a borehole and simultaneously measure NMR signals from an area near the borehole. With further reference to FIG. 2, in operation the apparatus is arranged to be rotated about its longitudinal axis 28 under power from a drilling apparatus (not shown) to cause the drilling means 22 to bore into the ground 30 at the situs of the geological structure sought to be analyzed, and thus form a borehole 32.

The NMR logging means 24 of this prior art device comprises a probe section made up of a permanent magnet 46, an antenna 48, and a control section 72 containing electronic/electrical components. A permanent magnet 46, shown in a cross-section in FIG. 2, generally has a tubular configuration and is designed to produce a gradient static magnetic field in the radial direction (i.e., outward from the longitudinal axis 28 of the tool). The static magnetic field of permanent magnet 46 has a field direction substantially perpendicular to the longitudinal axis 28, and a generally uniform amplitude along the azimuth with respect to that axis. This field is produced in a cylindrical region extending radially from the axis of the borehole 32.

The antenna 48 of the probe produces a RF magnetic field in the ground structure near the borehole to excite the nuclei of the materials sought to be analyzed. The direction of the RF magnetic field is substantially perpendicular to both the longitudinal axis of the apparatus and to the static field direction (stated in the Miller patent as one of the conditions for the proper operation of the device). The control section 72 comprises electronic/electrical components of the NMR logging means 24, designed to process NMR signals received from the sensitive region of the tool and to provide output signals indicative of the properties of the materials in this region.

In general, when lowered in a borehole, the probe section comprising logging means 24 is placed above the drilling means 22. It rotates with the drill bit about the longitudinal axis 28. Position stabilization means 26, in the form of fins, are provided on the side of the drilling means 22 to ensure that the position of the tool with respect to the borehole is stable. As is known in the art, in operation the entire tool is exposed to the high temperatures and extremely abrasive environment of the borehole. Thus, fins 26 serve in part to protect the apparatus 20 from hitting the walls of the borehole. Notably, however, in the prior art device illustrated in FIGS. 1–3 the fins do not extend to cover the logging means 24, which thus remains unprotected from direct contact with the walls of the borehole. For this reason, as further illustrated in FIG. 3, in the prior art the logging section is covered by a sleeve 70, which is preferably made of fiberglass, to protect the magnet and the antenna from these extreme conditions.

The present invention is directed to a modification of the geometry and configuration of prior art devices such as that illustrated in an exemplary embodiment in the Miller patent. A primary purpose of the modification is to provide high strength and abrasion resistance in a logging section of an NMR logging tool, while preserving the requisite orthogonality condition between the static magnet field generated by the permanent magnet(s) and the RF magnetic field generated by the antenna.

Figure 5:
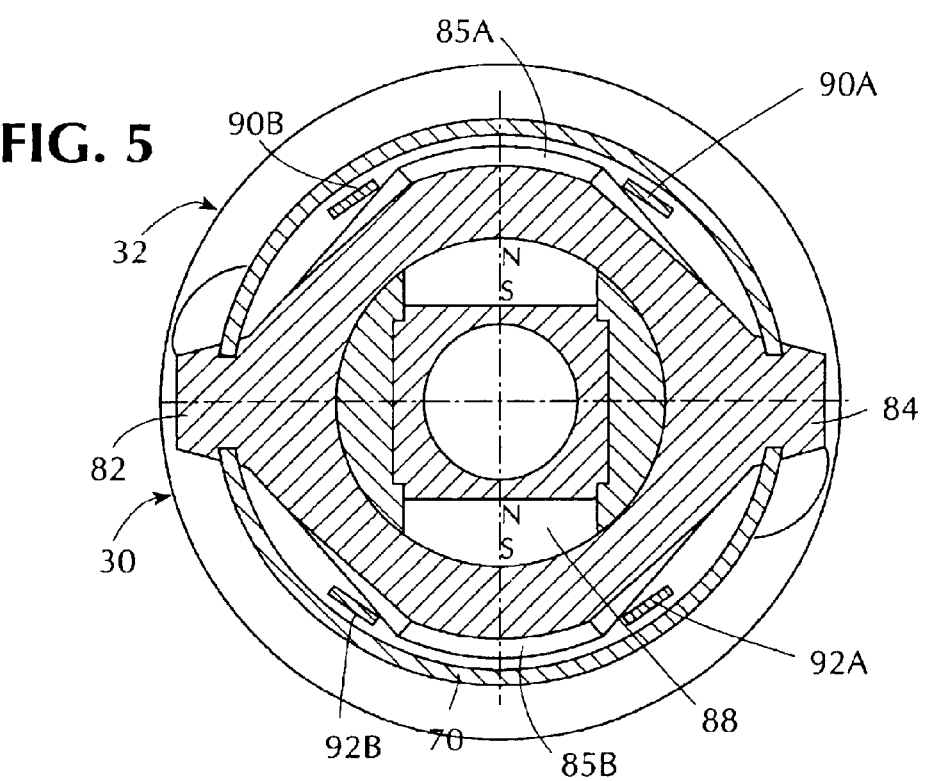
FIG. 5 is a cross-section of the probe section of the present invention, illustrating a non-magnetic collar with lateral protrusions, which act as wear pads.

Before discussing the details of the structure and operation of the probe shown in FIG. 5, it should be noted that in order to make magnetic resonance measurements of fluids, such as oil, in rock formations adjacent to a borehole by the use of a probe as described herein, three basic conditions must be satisfied.

The first condition is that the rotation of the drill must be well below the Larmor frequency. In a preferred embodiment, the Larmor frequency is in the range of one MHz, while the rate of tool rotation is less than ten Hz, and therefore the condition is always satisfied.

Figure 7:
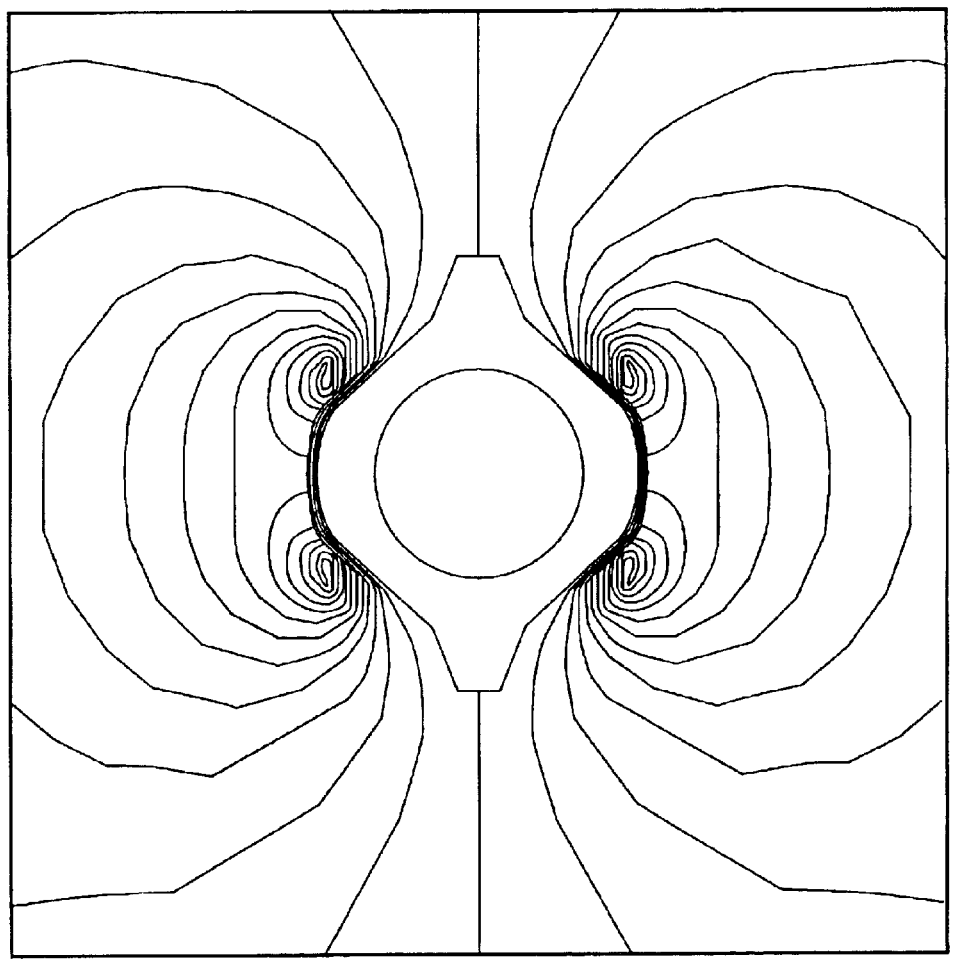
FIG. 7 illustrates a finite element model analysis showing the minimal effect of the metal collar protrusions on the RF magnetic field produced by the tool of the present invention.

The second condition is that electromagnetic radiation from the RF antenna must not be shielded on the outside by the collar forming the probe. In the case of metal collars, this condition typically means that the antenna must be placed outside the collar. This condition is necessary when the drill collar is electrically conductive because, as known in the art, electromagnetic waves do not propagate well through conductors. Furthermore, any additions to the collar, such as wings or wear pads, must not cause a significant distortion in the magnetic fields produced by the antenna. In FIG. 7, the effect of the addition of "wings" on the side of the collar section of the tool in a preferred embodiment of the invention has been modeled in two dimensions in a finite element analysis. This analysis shows the B1 field flux lines, and demonstrates that added wings have an insignificant effect on the overall magnetic field pattern produced by the RF antenna.

Figure 4:
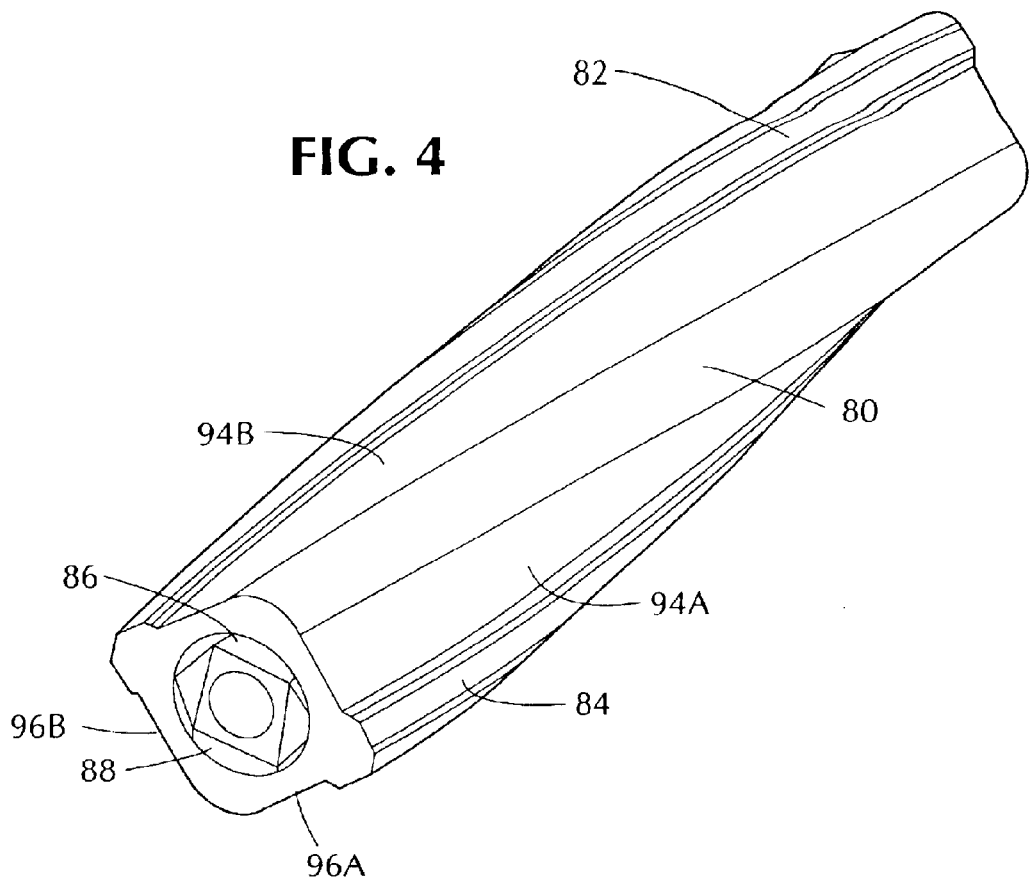
FIG. 4 is a three-dimensional view of the logging section in a preferred embodiment of the present invention.

The third basic condition that must be satisfied is that while the probe with the drilling means is rotated the static and RF magnetic fields produced by the probe must remain substantially orthogonal to each other in the formations near the borehole. This orthogonality condition is satisfied by a preferred probe configuration of this invention, because both the permanent magnet(s) and the RF antenna are twisted in the same direction and at the same twist angle. Thus, for any given cross-section, as shown in FIG. 5, the magnet(s) and the associated antenna have been rotated from the reference point by the same twist angle, thus preserving orthogonality. FIG. 4 shows the proposed collar geometry of this invention in 3-dimensions with the antennas, antenna soft-magnetic core, and external composite removed. FIG. 4 also shows the non-magnetic collar 80 with lateral extensions or "wings" 82 and 84, which provide increased abrasion resistance. Within the collar are one or more longitudinally disposed permanent magnets. In the embodiment shown in FIG. 4, two magnets 86 and 88 are disposed within the collar 80 on opposite sides of the collar. These magnets extend longitudinally the length of the probe section and are helically configured with the same longitudinal axis and twist angle as the overlying collar. Additionally, in FIG. 5, the soft magnetic antenna core 85A, and 85B, are also twisted similar to the antenna and magnet.

FIG. 4 illustrates in three-dimensions the collar geometry of the logging section used in a preferred embodiment of the present invention. Collar 80 is preferably made of a strong but non-magnetic alloy. In a preferred embodiment the collar is fabricated from an alloy, such as Inconel 718 made by Inco Alloy International at 3200 Riverside Drive, Huntington, W.Va. 25720. Other non-magnetic alloys could be used including, but not limited to, Monel metal or the alloy known as P-550, manufactured by Schoeller-Bleckmann in Ternitz, Austria. In FIG. 4 the collar has two lateral projections or "wings" 82 and 84. In the preferred embodiment the lateral protrusions 82 and 84 are manufactured as an integral part of the collar. Methods of manufacturing the collar with a helical twist and integral lateral projections are known in the art. For example, in one embodiment the entire collar could be made by milling or forging from a block of the alloy. However, other means of attaching lateral projections or wings to act as wear pads could be used. These include, but are not limited to, welding, bolting, riveting, or use of adhesives. It will be appreciated that the collar and the lateral projections may be made of the same or different materials.

Additionally, while in the embodiment illustrated in FIG. 4, two lateral projections 82 and 84 are provided along the length of the generally cylindrical collar 80, it will be appreciated that the number of lateral projections can vary.

In a preferred embodiment, magnets 86 and 88 are within the collar, as shown in FIG. 4 and FIG. 5. Preferably, two magnets are used that produce a dipole magnetic field with a magnetization axis substantially perpendicular to the longitudinal axis of the collar. In the illustrated embodiment these magnets extend the entire length of the collar section and preferably are made of samarium-cobalt alloy. The magnets are preferably configured in the form of a helix with the same direction of twist and angle of twist as the lateral projections (or wings) of the collar. It will be appreciated that the magnets can be made in a variety of configurations without departing from the scope of the invention. For example, the magnets may comprise magnet sections as described below. Other embodiments conforming with the generally helical overall shape of the apparatus of this invention may also be used, as will be appreciated by those of skill in the art.

The preferred embodiment shown in FIG. 4 also has two extended ribbons of magnetic material 86, 88 that are flat on one side and curved on the other. Other configurations include but are not limited to a single ribbon extending the length of the collar, or a single tubular magnet. In addition, more than two ribbon-shaped magnets may be used. In another embodiment, the magnet(s) may consist of short segments of magnet material placed end to end. Each segment is offset slightly in a circular direction, so as to form an overall helical configuration over the length of the probe. In a preferred embodiment these segments are about 2 inches long and are each offset by a sufficient amount to make a helix of the required degree of twist over the length of the collar.

In a preferred embodiment, illustrated in FIG. 4, two lateral projections 82 and 84 are provided along the length of the generally cylindrical collar 80. FIG. 4 shows an approximately 90° twist over the length of the collar. However, the degree of twist may be more or less than 90° with the twist angle produced by the helical rotation of the collar 80 and internal magnets 86 and 88 along the length of the probe section. In a preferred embodiment, wherein the non-magnetic collar has two "wings," as shown in FIG. 4, the degree of twist is 180° over the length of the collar. The degree of "twist" over the length of the probe section can vary, and the angle of twist can vary, as a function of distance along the probe section. However, in a preferred embodiment the angle of twist is uniform over the length of the probe and the metal collar 80, magnets 86 and 88, and antenna elements 90A, 90B, 92A, and 92B form a helix, whose longitudinal axis is the same as the longitudinal axis of the probe section.

Reference is now made to FIG. 5, which shows a cross-section of the drill collar of the present invention with lateral projections or wear-pads 82 and 84. It should be noted that this figure represents a cross-section of the "probe" section only of the logging tool. In a MWD tool this probe section would be part of an integrated package or assembly, which would also include drilling means and position stabilization means, all in an integrated package or assembly arranged to measure signals from a borehole, as it is being drilled. Thus, when the probe section in FIG. 5 is part of a measurement-while-drilling logging tool, it is rotated with the drilling means.

The probe section is made up of an assembly of permanent magnets 86 and 88 and antenna elements 90A, 90B, 92A, and 92B. The probe section is constructed to produce a gradient static magnetic field in the radial direction—that is, outward from the central longitudinal axis of the apparatus.

This magnetic field is produced in the geological structures 30 adjacent to the borehole 32. The probe also contains antenna elements 90A, 90B, 92A, and 92B, which serve to produce a radio frequency (RF) magnetic field in the ground structure adjacent to the borehole to excite nuclei of the materials sought to be analyzed. In the illustrated embodiment the antenna also serves to receive NMR signals from the materials sought to be analyzed. The output signals indicate the properties of the materials analyzed.

In one embodiment of the invention, the probe section has a non-magnetic collar with lateral projections or "wings" 82 and 84, as shown in cross-section in FIG. 5. These "wings" bear against the inside of the borehole 32 and provide the increased strength, rigidity and abrasion resistance needed to protect the probe section 24.

The helically configured permanent magnets 86 and 88 of the present invention produce a helical polarization in the region of the borehole adjacent to the probe section. The requirement that the magnetic field produced by the permanent magnets and the magnetic field produced by the RF magnetic field remain orthogonal is established in accordance with the invention by the helical configuration of the RF antennas over the length of the probe section. The antenna elements 90A, 90B, 92A, and 92B in a preferred embodiment occupy the depressions or troughs shown in FIG. 4 as 94A, 94B, 96A, and 96B. The direction of twist and twist angle of the RF antenna elements are identical to the direction of twist and twist angle of the one or more permanent magnets. Thus, any given cross-section through the probe section of the tool in a preferred embodiment would have the configuration shown in FIG. 5. It will be appreciated that sequential cross-sections taken at progressive points along the longitudinal axis of the probe section will be progressively displaced in a clockwise or counter-clockwise fashion.

In accordance with this invention, the total degree of displacement along the length of the probe section can vary. FIG. 4 shows an approximately 90° helical rotation of the collar and the internal magnet(s). In a preferred embodiment, the total displacement over the length of the probe section is 180°. The total degree of displacement or twist over the length of the probe section can be less than or greater than 180°. However, in the embodiment shown in the cross-section in FIG. 5, the non-magnetic collar has two lateral projections or "wings" 82 and 84, which function as wear pads. In this embodiment, a 180° twist will ensure that the wear pads will always be the first part of the probe section to contact the abrasive borehole wall during logging-while-drilling operations.

In operation the top surface of the wear pads 82 and 84 engages the wall of the borehole, thereby keeping the apparatus centered in the borehole and providing enhanced strength and abrasion resistance for the probe section 24. In addition, the probe section is covered with an abrasion resistant composite, such as fiberglass 70. The top surface of the wear pads 82 and 84 are level with or extend slightly above the surface of the composite, so that they bear against the abrasive walls of the borehole during rotation of the logging apparatus.

Referring now to FIG. 5, which shows a cross-section through the probe section of the present invention, the antenna elements 90A, 90B, 92A, and 92B have a configuration similar to the antenna elements shown in the prior art probe section depicted in FIG. 3. In FIG. 3, the antenna elements are labeled 52A, 52B, 54A, and 54B. The antenna elements of the present invention are of the same general size and configuration. However, they are twisted over the length of the probe section at the same twist angle as the metal collar 80 and magnets 86 and 88, as shown in both FIG. 4 and FIG. 5. In a preferred embodiment of the present invention the antenna elements 90A, 90B, 92A, and 92B occupy the depressions or troughs in the non-magnetic collar shown as 94A, 94B, 96A, and 96B in FIG. 4.

As noted, the antenna elements 90A, 90B, 92A, and 92B serve as the means for creating the RF field in the sensitive volume in order to excite the nuclei of the materials sought to be analyzed. In addition, the antenna element serves as the means for receiving NMR signals produced by the excited nuclei. With reference to FIG. 3, the antenna 50 serves as a calibration antenna—i.e., the antenna and associated electronics (not shown) effect the measurement of the electrical loading of the environment in order to calibrate the system. The details of the construction and arrangement of the antenna elements 90A, 90B, 92A, and 92B will best be understood by reference to FIGS. 3, 4, and 5. As one can see, the antenna comprises two pairs of parallel connected conductors. FIG. 3 shows the antenna configuration disclosed in the Miller patent with the two pairs 52 and 54 connected in series with each other to form a series/parallel antenna 48. The series/parallel antenna 48 is connected to associated electronic/electrical components of the system (e.g., a RF transmitter/receiver (not shown)).

In the present invention, the two pairs of conductors are labeled 90A, 90B, 92A, and 92B. These two pairs of conductors, in accordance with a preferred embodiment of the invention, are in the form of a thin strip of conducting material, such as copper, and have a width that constitutes in a preferred embodiment approximately 16 degrees of the circular periphery of the collar 80 upon which the antenna is mounted. The four strips or conductors 90A, 90B, 92A, and 92B making up the antenna run the length of the collar section 80 in the helically configured troughs or depressions shown as 94A, 94B, 96A, and 96B in FIG. 4. The angular distance separating the conductors 90A and 90B from each other is approximately 20 degrees. In a preferred embodiment, the conductors 92A and 92B are similarly constructed and oriented with respect to each other. The conductors 90A, 90B, 92A, and 92B are electrically connected at one end to a ring conductor 56 (see FIG. 3). The conductors 90A and 90B are electrically connected to each other by a bridging conductor 58. In a similar manner, the other ends of conductors 92A and 92B are electrically connected to each other by a bridging conductor 60. The bridging conductor is electrically connected to a central conductor 62A of a coaxial cable 62, while the bridging conductor 60 is electrically connected to a braided wire conductor 62B.

The two conductor pairs 90A, 90B, 92A, and 92B are preferably mounted on the collar 80 at diametrically opposed positions with respect to each other (see FIGS. 4 and 5). In particular, conductor pair 90 is disposed along the north pole of magnet 86, while conductor pair 92 is disposed along the south pole of magnet 88.

Figure 6:
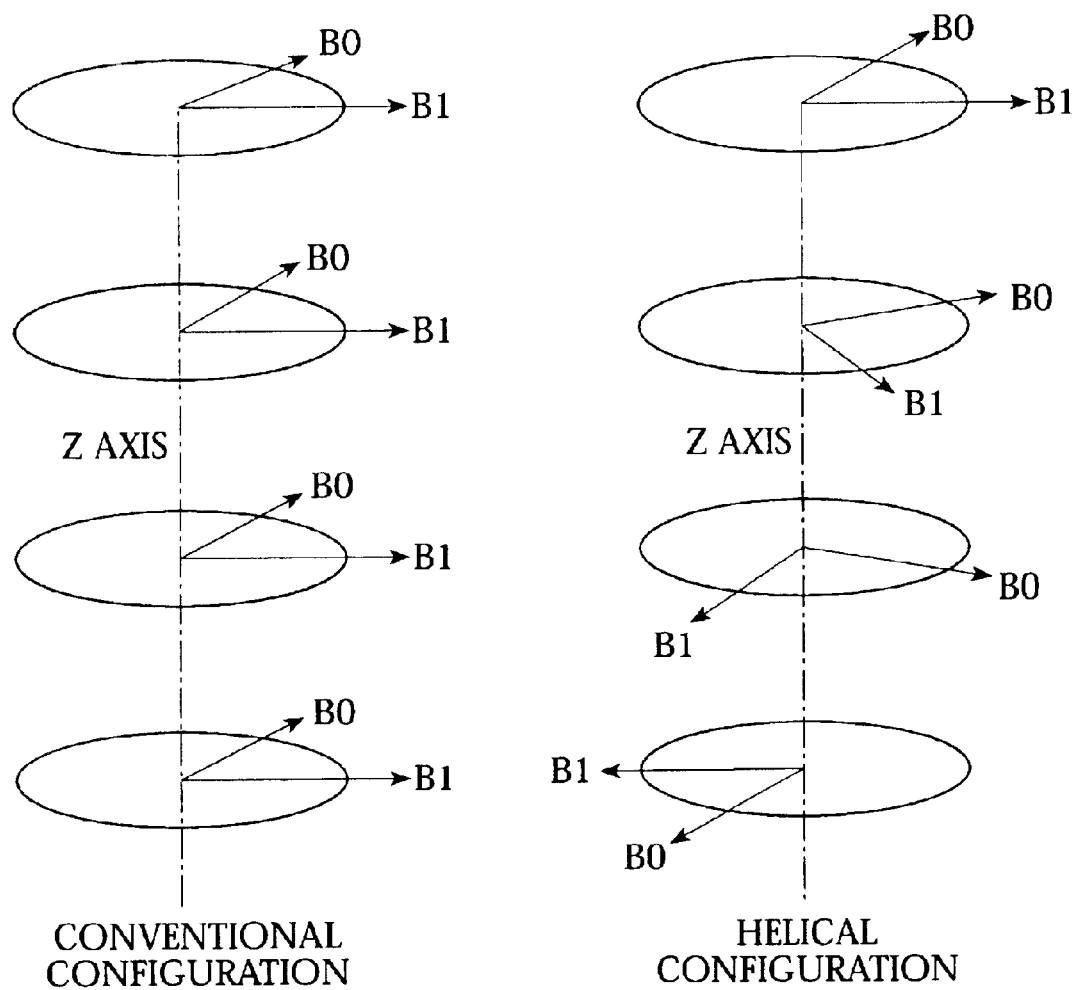
FIG. 6 is a schematic comparison of static and radio frequency magnetic fields in the prior art versus the helical configuration of the present invention. In both the conventional and helical configuration, the B0 and B1 fields are perpendicular.

The conductors pairs 90A, 90B, 92A, and 92B follow the helical depressions 94A, 94B, 96A, and 96B shown in FIG. 4, so that the RF magnetic field produced by the conductors remains substantially orthogonal to the helically polarized static magnetic field produced by magnets 88 and 86, as shown in FIG. 6.

As mentioned above, the antenna is connected to a transmitter/receiver. In particular, the conductor 62A is connected to a positive potential output/input terminal (designated by the "+" in FIG. 3) of the RF transmitter/receiver, while the conductor 62B is connected to ground. The transmitter/receiver may be of any suitable construction for producing the desired electrical signals to excite the nuclei of the material(s) in the sensitive volume and for providing electrical output signals representative of the NMR signals produced by the excited nuclei.

The calibration antenna 50 used in a preferred embodiment is generally a small antenna that comprises a twisted pair of thin electrical conductors 50A terminating at a looped end 50B. One of the conductors 50A is electrically connected to the central conductor 64A of another coaxial cable 64, while the other of the conductors 50A is electrically connected to the braided wire conductor 64B of that cable. The cable 64 is connected to suitable calibration circuitry (not shown) located within the collar section in which other electronic/electrical components making up the system 20 are located. Thus, the braided conductor 64B of the cable is connected to ground and the conductor 64A is connected to a positive potential terminal (designated by the "+" in FIG. 3) of the calibration circuitry.

The electronic/electrical components that make up the system 20 (see FIG. 1) (e.g., the transmitter/receiver, controller, etc.) are located within a "control" collar section 72.

The following section provides a mathematical analysis establishing that the static magnetic field produced by the helically configured permanent magnet(s) and the alternating (RF) magnetic field produced by the correspondingly configured antennas maintain the required substantial orthogonality over the length of the probe section. The mathematical relations given below describe the influence of the magnet and antenna dimensions, angle of twist, and magnetization direction on the Signal to Noise Ratio of the described twisted NMR system relative to the regular 'untwisted' configuration.

Theoretical Background

SNR Relative Estimation

One of the major indicators of the efficiency of an NMR sensor is its Signal to Noise Ratio (SNR). The higher the SNR, the higher the quality of the obtained data. To prove feasibility of the Helical Polarization NMR tool further, the SNR relative estimation method is used to show that the tool's twisting (of up to about 6° per inch) does not decrease the SNR of the basic untwisted tool.

Diverse expressions for SNR estimation are described in the literature. Various parameters in these expressions can be divided into three main categories: fundamental constants, sample properties, and tool parameters. Many of the parameters categorized as "sample properties" and "tool parameters" can be evaluated only approximately, so that the SNR estimation error can go as high as tens of percents.

SNR estimation becomes even more complicated when NMR signals are evaluated from non-uniform samples under inhomogeneous B0 and B1 fields, as with the MRIL® tool made by NUMAR. Therefore, since to obtain reliable results, in the following discussion we will not consider the SNR absolute value evaluation for a "twisted" MRIL® tool, but rather the NMR signal's relative change as a function of twist angle $\tau$.

Consequently, we will compare an SNR obtained from an untwisted NMR tool, "the basic SNR", with the SNR of "the twisted tool," which is a modification of the basic tool obtained as a result of twisting along its axis on the twist angle $\tau$.

It will be clear to a person of ordinary skill in the art that such a twisting of the magnet and antenna will cause changes in the B0 and B1 fields within a sample formation. In this analysis, these changes are taken into account by using the expressions for the B0 and B1 given below. Thus, the shape and volume of the sensitive volume ($V_S$) will change, while the Larmor frequency $\omega_0$, and therefore the B0 amplitude, will remain constant for each twisted tool not dependent on $\tau$. Furthermore, twisting will cause a slight change in the antenna's quality factor, antenna's active resistance, and inductance.

It is evident that for the SNR's relative evaluation, the following parameters remain unchanged: sample properties, temperature, Larmor frequency, pulse sequence, transceiver parameters, wire conductivity, etc. (not to mention fundamental constants). Thus, they can be omitted while SNR relative analysis is performed.

In this analysis, the tools under comparison do not include oversaturated elements, but may include non-linear elements (e.g., soft ferrite). It is assumed that any non-linear elements are working within the linear range of their characteristics (e.g., BH curves). This assumption enables the use of the Principle of Reciprocity for SNR evaluation. See D. I. Hoult and R. E. Richards, "The signal-to-noise of the nuclear magnetic resonance experiment," J. Magn. Reson. 24:71–85 (1976).

Thus, the main parameters that related to SNR and influenced by twisting are: $\vec{B0}$, $\vec{B1}$, $V_s$. Accordingly, the following expression is defined for an estimation of the twisting effect on SNR of NMR sensor:

$$SNR(\tau) \propto \sum_{i=1}^{n} [B1_i^{(\perp B0)} \cdot V_{Si}] \cdot \sin\left(\frac{B1_i^{(\perp B0)}}{B1(90°, \tau)} \cdot \frac{\pi}{2}\right) \quad (1)$$

where B1(90°, τ) is twisted tool 90° pulse amplitude;

$B_{1_i}^{(\perp B0)}$ is the $\vec{B1}$ projection onto the plane perpendicular to $\vec{B0}$ within the i-volume of the sensitive volume ($V_{Si}$);

$$\sin\left(\frac{B1_i^{(\perp B0)}}{B1(90°, \tau)} \cdot \frac{\pi}{2}\right)$$

is a flip angle factor taking into account a RF pulse deviation from 90° pulse within i-volume, which results in an imperfect tipping of protons; and n is the number of elementary volumes by which a sensitive volume was divided.

Static Field Estimation

In the following analysis use is made of well known expressions for a magnetic vector potential A and the magnetic induction vector B for finding mathematical relations between magnets' properties and produced magnetic field. In particular, the magnetic vector potential is given by the expression:

$$\vec{A} = \int_V \frac{[\vec{M} \times \vec{R}]}{R^3} dV \quad (2)$$

where M is a vector of a domain magnetization
R is a radius vector from a domain to a target point, and
V is magnet volume. The magnetic induction vector is given by the expression:

$$\vec{B} = \text{rot}\vec{A} \quad (3)$$

Figure 8:
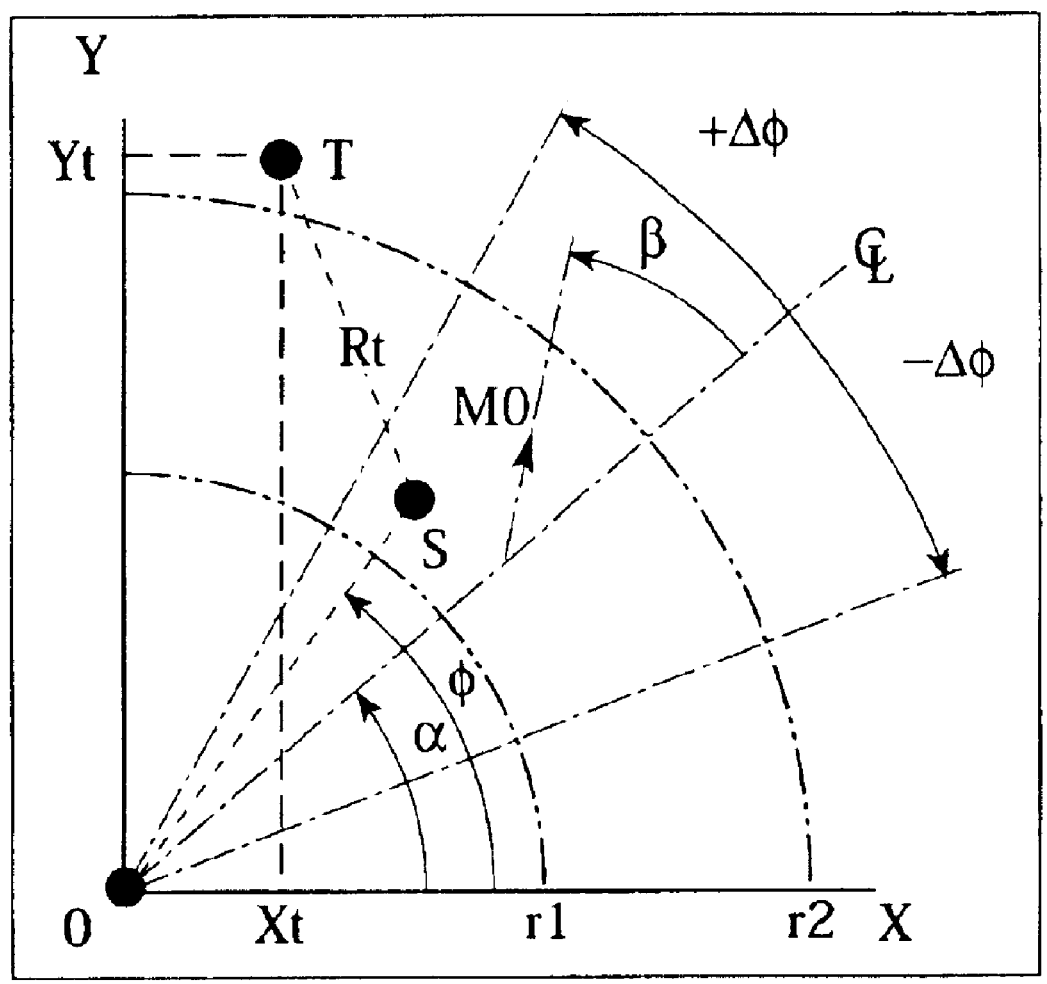
FIG. 8 shows a partial cross-section with parameters for the theoretical mathematical analysis of a twisted magnetic cylinder, used in accordance with the present invention.

With reference to FIG. 8, the elementary magnetic system has the shape of a ring segment (in a cross section) twisted by the angle τ along the magnet length L, according to the following notation:

α—center line angle—an angle between the X-axis and a center line of a segment cross-section;

β—magnetization angle—an angle between a center line and a vector of magnetization M;

2ΔΦ—central angle of the segment;

Rt—radius-vector from the point S (a source of magnetic field) to the point T (target point) with coordinates (Xt, Yt, Zt);

r1 and r2—inner and outer segment radiuses; and r, Φ, z—attributes of cylindrical coordinate system.

The twist angle τ is constant and is related to magnet length L by the expression $$\tau = t \cdot L \quad (4)$$

where t is a twist coefficient (for example, at $$\tau = \frac{\pi}{2},$$

as shown in FIG. 8, $$t = \frac{\pi}{2 \cdot L}$$

The center line angle α depends on coordinate Z and is defined as $$\alpha = t \cdot Z + \alpha 0 \quad (5)$$

where α0 is angle α at the center of magnet length (Z=0).

Taking into account the above, the following expressions can be obtained for the Magnetic Flux Density components at the point T (Xt, Yt, Zt):

$$Bx(\alpha 0, \Delta\varphi, \beta) := \int_{-L/2}^{L/2} \int_{z \cdot t + \alpha 0 - \Delta\varphi}^{z \cdot t + \alpha 0 + \Delta\varphi} \int_{r1}^{r2} \frac{M0}{1000} \cdot \left[ 2 \cdot \frac{\cos(t \cdot z + \alpha 0 + \beta)}{\left[\sqrt{(Xt - r \cdot \cos(\varphi))^2 + (Yt - r \cdot \sin(\varphi))^2 + (Zt - z)^2}\right]^3} \cdot 3 \cdot \frac{\cos(t \cdot z + \alpha 0 + \beta) \cdot [(Yt - r \cdot \sin(\varphi))^2 + (Zt - z)^2] - }{\sin(t \cdot z + \alpha 0 + \beta) \cdot (Xt - r \cdot \cos(\varphi)) \cdot (Yt - r \cdot \sin(\varphi))} \right] \cdot r \, dr \, d\varphi \, dz \quad (6)$$

$$By(\alpha 0, \Delta\varphi, \beta) := \int_{-L/2}^{L/2} \int_{z \cdot t + \alpha 0 - \Delta\varphi}^{z \cdot t + \alpha 0 + \Delta\varphi} \int_{r1}^{r2} \frac{M0}{1000} \cdot \left[ 2 \cdot \frac{\sin(t \cdot z + \alpha 0 + \beta)}{\left[\sqrt{(Xt - r \cdot \cos(\varphi))^2 + (Yt - r \cdot \sin(\varphi))^2 + (Zt - z)^2}\right]^3} \cdot 3 \cdot \frac{\sin(t \cdot z + \alpha 0 + \beta) \cdot [(Xt - r \cdot \cos(\varphi))^2 + (Zt - z)^2] - }{\cos(t \cdot z + \alpha 0 + \beta) \cdot (Yt - r \cdot \sin(\varphi)) \cdot (Xt - r \cdot \cos(\varphi))} \right] \cdot r \, dr \, d\varphi \, dz \quad (7)$$

-continued $$Bz(\alpha 0, \Delta\varphi, \beta) := \int_{-\frac{L}{2}}^{\frac{L}{2}} \int_{z \cdot t + \alpha 0 - \Delta\varphi}^{z \cdot t + \alpha 0 + \Delta\varphi} \int_{r1}^{r2} \frac{M0}{1000} \cdot \left[ 3 \cdot (Zt - z) \cdot \frac{\cos(t \cdot z + \alpha 0 + \beta) \cdot (Xt - r \cdot \cos(\varphi)) + \sin(t \cdot z + \alpha 0 + \beta) \cdot (Yt - r \cdot \sin(\varphi))}{\left[\sqrt{(Xt - r \cdot \cos(\varphi))^2 + (Yt - r \cdot \sin(\varphi))^2 + (Zt - z)^2}\right]^5} \right] \cdot r \, dr \, d\varphi \, dz \quad (8)$$

where M0 is an amplitude of a magnet magnetization (corresponds to Hc for SmCo).

A few important cases of using equations (6), (7), (8) are discussed below.

Figure 9A:
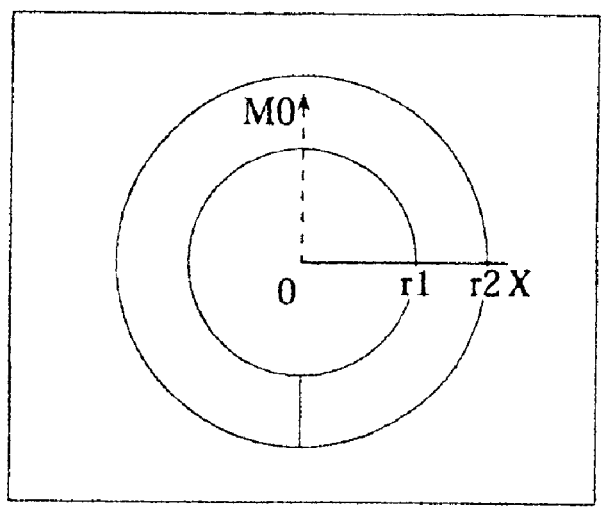
FIG. 9A shows the cross-section of a regular magnetic cylinder with diametrical direction of magnetization.
Figure 9B:
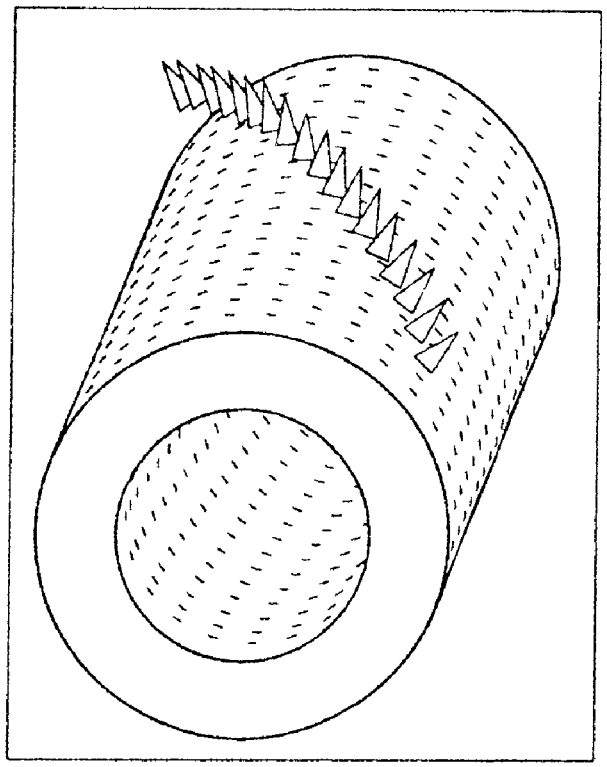
FIG. 9B shows magnetic field produced by a twisted magnetic cylinder.

Regular Magnetic Cylinder Case (not twisted) (see FIG. 9A):

$\tau=0, t=0; \Delta\Phi=\pi; \alpha 0=\pi/2; \beta=0.$ (2) Twisted Magnetic Cylinder Case (see FIG. 9B):

$$\tau = \frac{\pi}{2}, t = \frac{\pi}{(2L)};$$

Figure 10A:
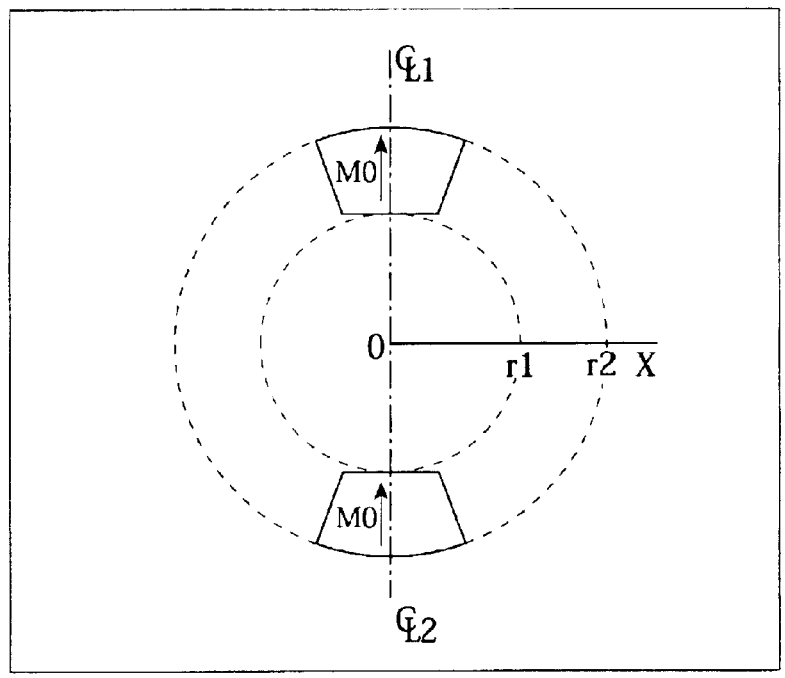
FIG. 10A shows a two magnet configuration used in a preferred embodiment of the present invention.

$\Delta\Phi=\pi; \alpha 0=\pi/2; \beta=0.$ (3) Two Magnets Case (see. FIG. 10A):
Magnet 1:

$$\tau = \frac{\pi}{2}, t = \frac{\pi}{(2L)};$$

$\Delta\Phi=\text{constant}; \alpha 0=\pi/2; \beta=0.$

Magnet 2:

$$\tau = \frac{\pi}{2}, t = \frac{\pi}{(2L)};$$

$\Delta\Phi=\text{constant}; \alpha 0=3/2\pi; \beta=\pi.$ $$r1 \Rightarrow \frac{r1}{\cos\varphi\cos(t \cdot z + \alpha 0) + \sin\varphi\sin(t \cdot z + \alpha 0)}$$

Bx=Bx1+Bx2
By=By1+By2
Bz=Bz1+Bx2

Figure 10B:
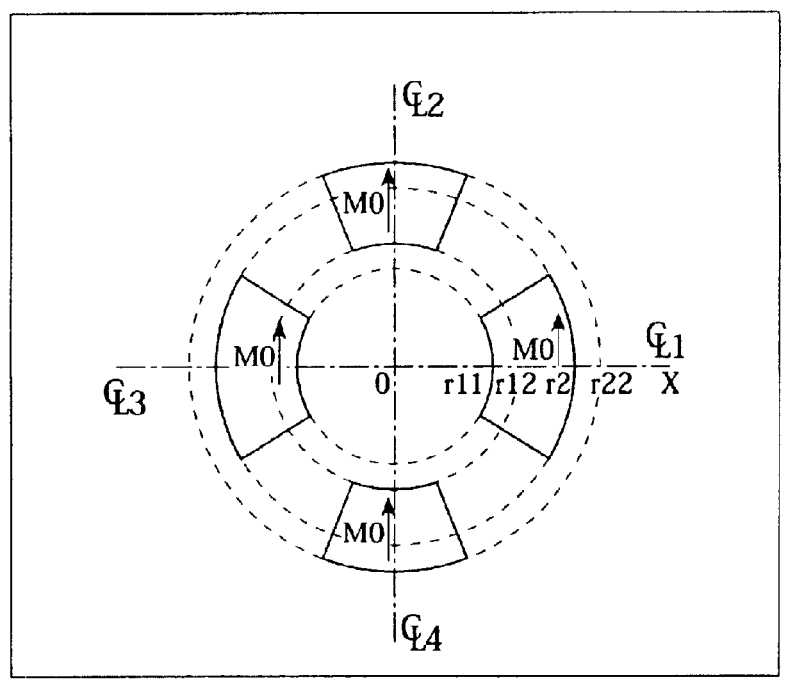
FIG. 10B shows a four magnet configuration.

(4) Four Magnets Case (see FIG. 10B):

Bx=Bx1+Bx2+Bx3+Bx4
By=By1+By2+By3+By4
Bz=Bz1+Bz2+Bz3+Bz4

Calculation Examples

A variation of a polarization field of a magnetic cylinder before "twisting" (Regular Cylinder Case: t=0) and after "twisting" it by the angle of $\tau=\pi/2$ (Twisted Cylinder Case: $t=\pi/(2L)$ has been considered. The following parameter values were used: r1=1.2", r2=2", L=52", M0=790000 A/m, $\alpha 0=\pi/2$, $\Delta\Phi=\pi$, and the sensitive radius is 6.75". The calculation results are shown in Tables 1 and 2 below and in graph form in FIG. 11 and FIG. 12.

Figure 11:
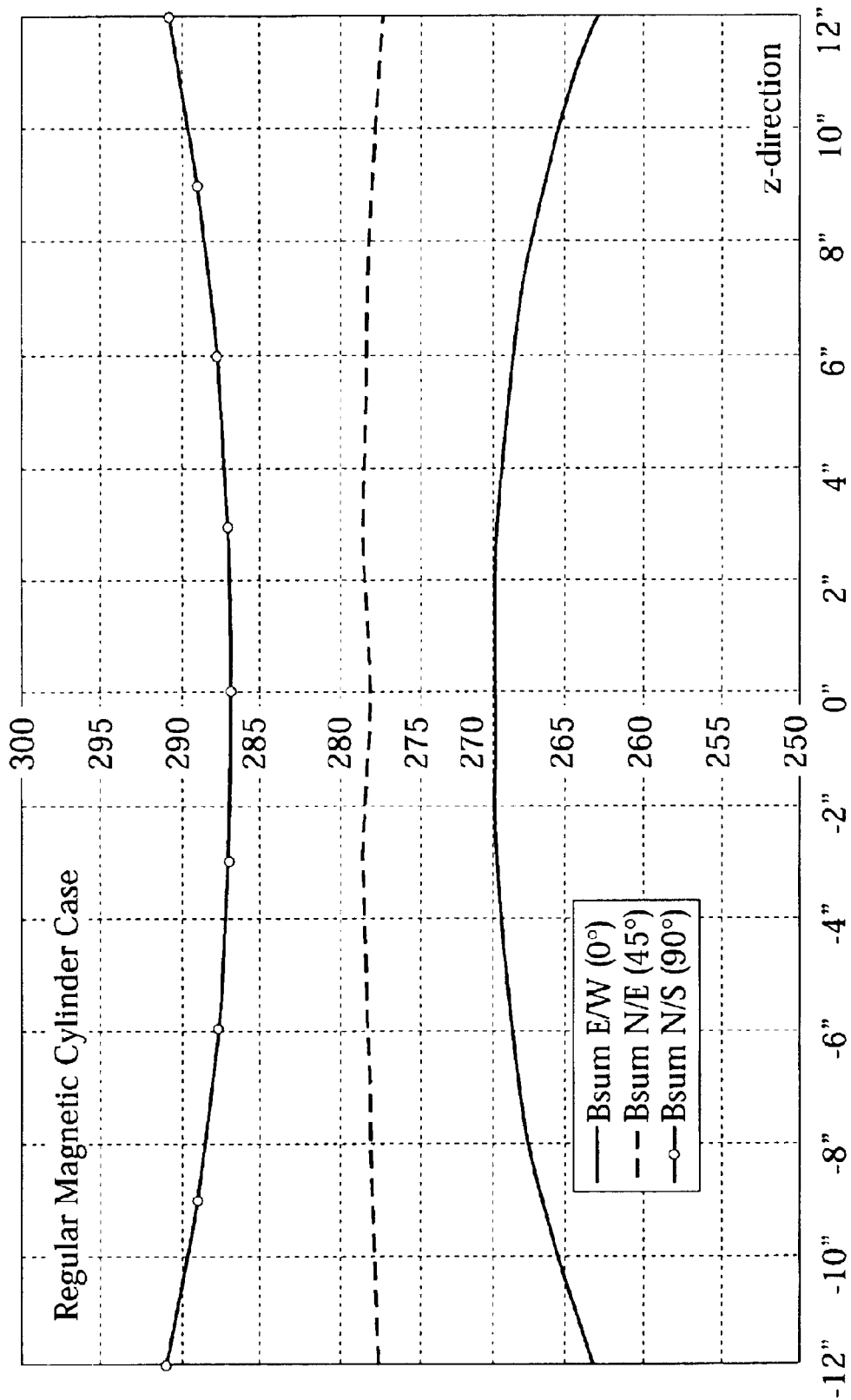
FIG. 11 shows a graph of magnetic field intensity ($B_{sum}$) as a function of distances along the longitudinal axis of a non-twisted magnetic cylinder.
Figure 12:
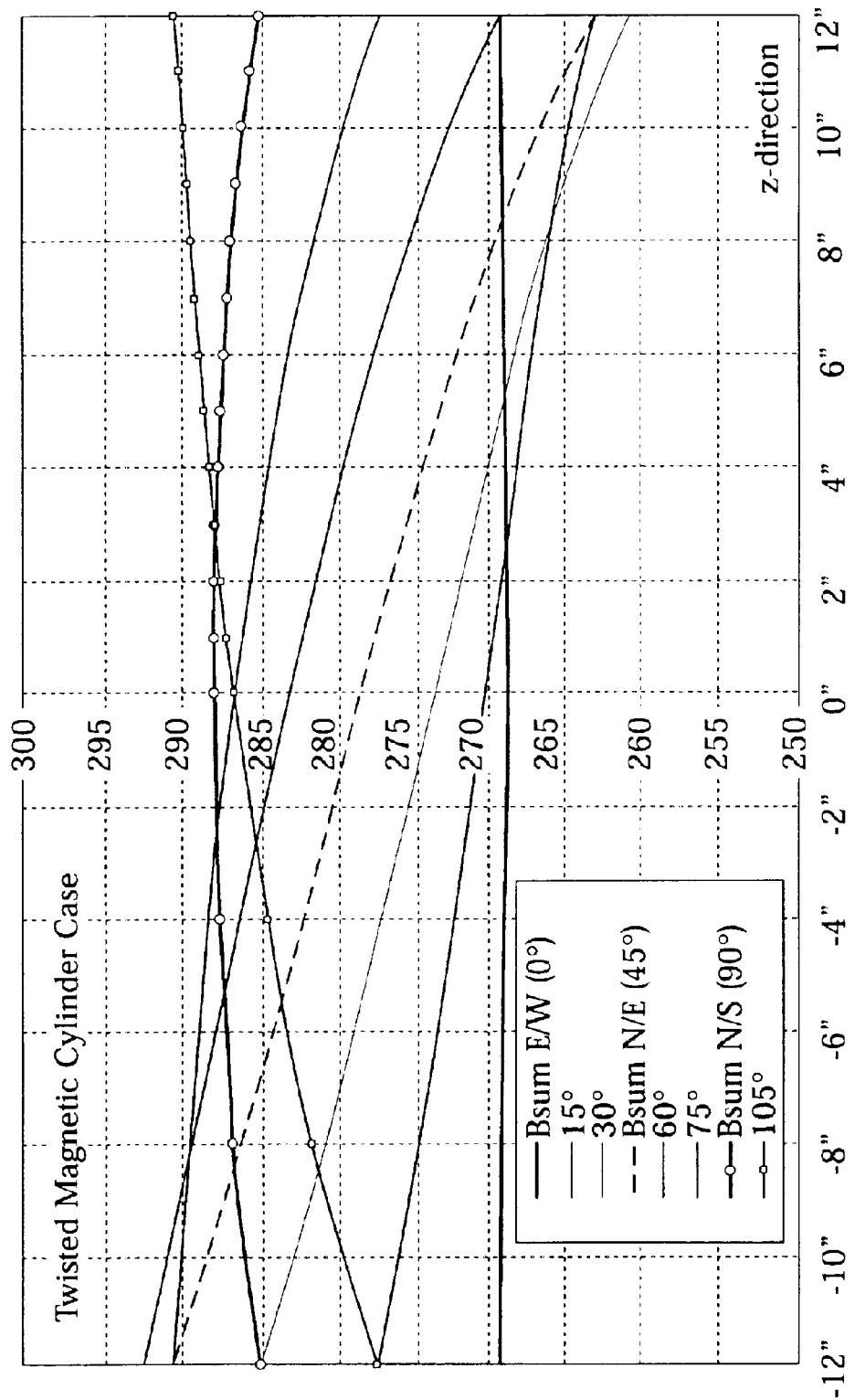
FIG. 12 shows graph of magnetic field intensity (Bsum) as a function of distances along the longitudinal axis for twisted (helical) magnetic cylinder, used in accordance with the present invention.

The graph in FIG. 11 shows the magnetic field at the antenna zone for an untwisted magnetic cylinder and the graph in FIG. 12 shows the magnetic field calculated to be produced by the helically-configured or twisted magnetic cylinder.

FIG. 12 shows, in graph form, the results of a numerical integration of Equations (6), (7) and (8) for the idealized case of a helically-twisted magnetic cylinder. The lines show Bsum (total magnetic field intensity) at various orientations over the length of the twisted magnetic cylinder. Comparison to FIG. 11 (the untwisted cylinder) shows that after twisting of the cylinder the ellipticity of the magnetic field has changed very little.

Figure 13A:
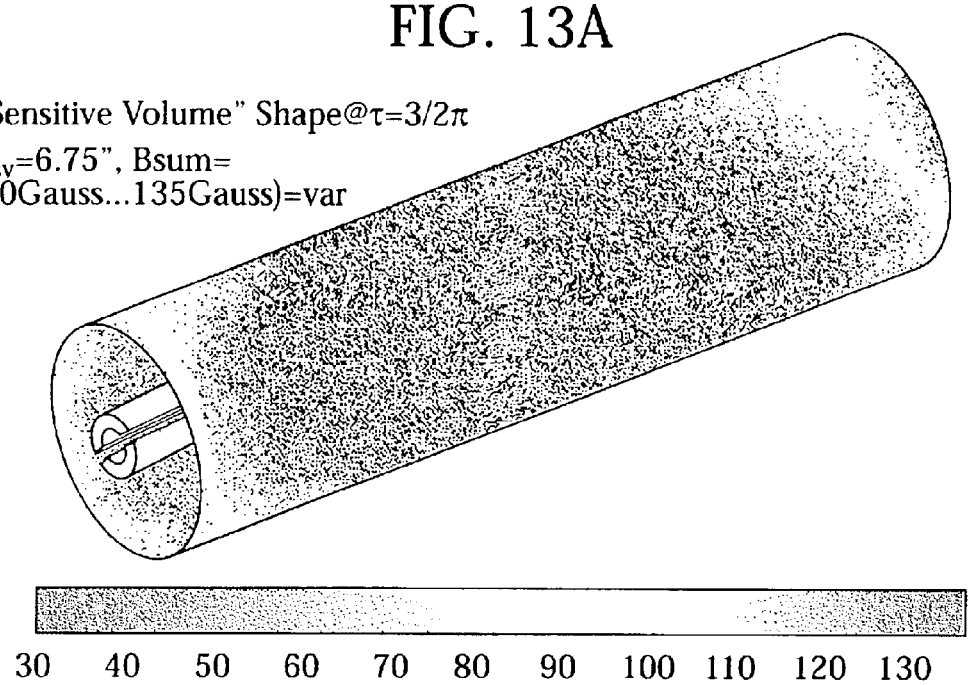
FIG. 13A shows the static field intensity of the twisted magnetic cylinder with twist angle of $3/2\pi$.
Figure 13B:
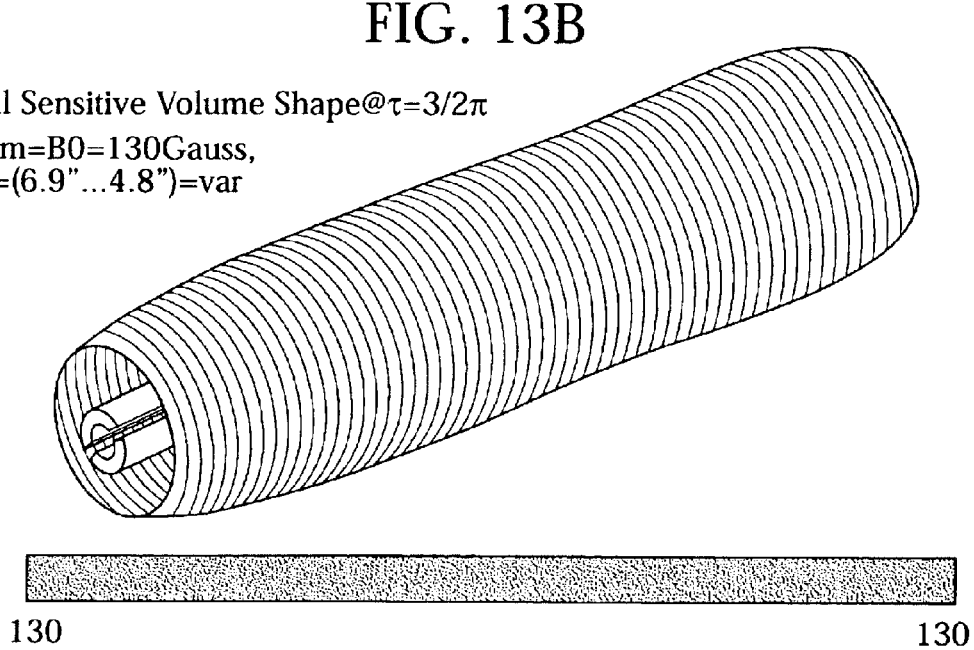
FIG. 13B shows a sensitive volume shape for the twisted magnetic cylinder with twist angle of $3/2\pi$.

FIG. 13A and FIG. 13B show the results of the static field simulations of the twisted by $\tau=3/2\pi$ magnet by using the equations (6), (7), and (8). As shown in FIG. 13A, at the fixed radius (6.75"), the static field intensity varies in a wide range, from 30 to 140 Gauss, along the entire magnet length. However, the variation of the field in the middle portion of the magnet (about ⅓ of the magnet length), which is typically used as an NMR sensitive volume and where antenna is located, is similar to that of the untwisted magnet. FIG. 13B shows that, at fixed field intensity (130 Gauss), the spatial variation of the sensitive volume shape at the middle portion of the magnet is very close to the ideal cylinder of about 6.75" radius.

This mathematical model and the calculated field intensities are intended only to illustrate that the probe section of a downhole measurement-while-drilling NMR apparatus can be twisted to produce a helically configured magnet and still retain substantial orthogonality between the static magnetic field and the radio frequency (RF) magnetic field produced by the antenna so that NMR measurements of the

| Magnet 1: | Magnet 2: | Magnet 3: | Magnet 4: |
|---|---|---|---|
| $\tau = \pi/2, t = \pi/(2L)$ | $\tau = \pi/2, t = \pi/(2L)$ | $\tau = \pi/2, t = \pi/(2L)$ | $\tau = \pi/2, t = \pi/(2L)$ |
| $\Delta\varphi = \text{const1}$ | $\Delta\varphi = \text{const2}$ | $\Delta\varphi = \text{const1}$ | $\Delta\varphi = \text{const2}$ |
| $\alpha 0 = 0$ | $\alpha 0 = \pi/2$ | $\alpha 0 = \pi$ | $\alpha 0 = 3/2\pi$ |
| $\beta = \pi/2$ | $\beta = 0$ | $\beta = -\pi/2$ | $\beta = \pi$ |
| r1 = r11 | r1 = r12 | r1 = r11 | r1 = r12 |
| r2 = r21 | r2 = r22 | r2 = r21 | r2 = r22 | region surrounding the probe can be made. FIG. 6 shows a comparison of the direction of the static magnetic field Bo and the induced or radio frequency magnetic field B1 for the conventional dipole configuration, as in the prior art device, and the helically configured fields produced by a twisted magnet of the probe section of the present invention.

TABLE 1

Regular Magnetic Cylinder Case

|  | −12" | −9" | −6" | −3" | 0" | 3" | 6" | 9" | 12" |
|---|---|---|---|---|---|---|---|---|---|
| BsumE/W (0°) | 263.1 | 266.6 | 268.6 | 269.7 | 270.0 | 269.7 | 268.6 | 266.6 | 263.1 |
| BsumN/E (45°) | 277.4 | 278.1 | 278.4 | 278.5 | 278.1 | 278.5 | 278.4 | 278.1 | 277.4 |
| BsumN/S (90°) | 291.0 | 289.1 | 287.8 | 287.2 | 287.0 | 287.2 | 287.8 | 289.1 | 291.0 |
| Bx |  |  |  |  |  |  |  |  |  |
| 0° | 0.0 | 0.0 | 0.0 | 0.0 | 0.0 | 0.0 | 0.0 | 0.0 | 0.0 |
| 45° | 277.0 | 277.8 | 278.2 | 278.4 | 278.0 | 278.4 | 278.2 | 277.8 | 277.0 |
| 90° | 0.0 | 0.0 | 0.0 | 0.0 | 0.0 | 0.0 | 0.0 | 0.0 | 0.0 |
| By |  |  |  |  |  |  |  |  |  |
| 0° | −263.1 | −266.6 | −268.6 | −269.7 | −270.0 | −269.7 | −268.6 | −266.6 | −263.1 |
| 45° | 13.8 | 11.2 | 9.6 | 8.8 | 8.5 | 8.8 | 9.6 | 11.2 | 13.8 |
| 90° | 290.8 | 289.0 | 287.8 | 287.2 | 287.0 | 287.2 | 287.8 | 289.0 | 290.8 |
| Bz |  |  |  |  |  |  |  |  |  |
| 0° | 0.0 | 0.0 | 0.0 | 0.0 | 0.0 | 0.0 | 0.0 | 0.0 | 0.0 |
| 45° | 7.3 | 4.2 | 2.3 | 1.0 | 0.0 | 1.0 | 2.3 | 4.2 | 7.3 |
| 90° | 10.4 | 5.9 | 3.3 | 1.5 | 0.0 | 1.5 | 3.3 | 5.9 | 10.4 |

TABLE 2

Twisted Magnetic Cylinder Case

| | -12" | -8" | -4" | 0" | 1" | 2" | 3" | 4" | 5" | 6" | 7" | 8" | 9" | 10" | 11" | 12" |
|---|---|---|---|---|---|---|---|---|---|---|---|---|---|---|---|---|
| BsumE/W (0°) | 269.2 | 269.1 | 268.9 | 268.8 | 268.8 | 268.8 | 268.8 | 268.9 | 269.0 | 269.1 | 269.1 | 269.1 | 269.2 | 269.2 | 269.2 | 269.2 |
| 15° | 277.3 | 274.6 | 272.2 | 270.1 | 269.6 | 269.1 | 268.6 | 268.2 | 267.7 | 267.2 | 266.7 | 266.1 | 265.5 | 264.8 | 264.1 | 263.2 |
| 30° | 285.1 | 280.9 | 277.7 | 273.7 | 272.9 | 272.0 | 271.2 | 270.3 | 269.4 | 268.4 | 267.4 | 266.4 | 265.2 | 264.0 | 262.6 | 261.1 |
| 60° | 290.7 | 286.3 | 282.5 | 278.6 | 277.6 | 276.7 | 275.6 | 274.6 | 273.5 | 272.4 | 271.2 | 269.9 | 268.5 | 266.9 | 265.3 | 263.4 |
| 75° | 292.8 | 289.6 | 286.6 | 283.4 | 282.6 | 281.7 | 280.8 | 279.9 | 278.9 | 277.9 | 276.8 | 275.6 | 274.3 | 272.8 | 271.2 | 269.5 |
| BsumN/S (90°) | 290.8 | 289.8 | 288.8 | 286.9 | 286.4 | 285.9 | 285.3 | 284.7 | 284.1 | 283.4 | 282.7 | 281.8 | 280.9 | 279.9 | 278.8 | 277.5 |
| 105° | 285.3 | 287.0 | 287.9 | 288.2 | 288.1 | 288.1 | 288.0 | 287.9 | 287.7 | 287.6 | 287.3 | 287.0 | 286.7 | 286.3 | 285.9 | 285.3 |
| BXX | 277.5 | 281.8 | 284.7 | 286.9 | 287.3 | 287.8 | 288.2 | 288.6 | 288.9 | 289.3 | 289.6 | 289.9 | 290.2 | 290.4 | 290.6 | 290.8 |
| 0° | 107.9 | 72.3 | 36.3 | 0.0 | -9.1 | -18.2 | -27.2 | -36.3 | -45.3 | -54.3 | -63.3 | -72.3 | -81.3 | -90.2 | -99.1 | -107.9 |
| 15° | 223.6 | 197.4 | 168.8 | 138.0 | 130.0 | 121.8 | 113.5 | 105.1 | 96.6 | 88.0 | 79.2 | 70.3 | 61.3 | 52.2 | 43.0 | 33.6 |
| 30° | 282.4 | 271.4 | 257.0 | 239.1 | 234.0 | 228.7 | 223.3 | 217.5 | 211.6 | 205.4 | 199.0 | 192.3 | 185.4 | 178.2 | 170.8 | 163.1 |
| 45° | 268.6 | 274.5 | 277.2 | 276.0 | 275.1 | 274.0 | 272.5 | 270.8 | 268.8 | 266.5 | 263.9 | 260.9 | 257.7 | 254.1 | 250.1 | 245.8 |
| 60° | 185.9 | 205.9 | 233.9 | 239.1 | 242.3 | 245.3 | 248.1 | 250.6 | 252.9 | 254.6 | 256.5 | 257.8 | 258.8 | 259.5 | 259.7 | 259.6 |
| 75° | 56.4 | 83.9 | 111.5 | 138.0 | 144.4 | 150.5 | 156.6 | 162.4 | 168.1 | 173.6 | 178.8 | 183.8 | 188.5 | 193.0 | 197.0 | 200.7 |
| 90° | -85.1 | -58.7 | -29.9 | 0.0 | 7.5 | 15.0 | 22.5 | 29.9 | 37.2 | 44.5 | 51.7 | 58.7 | 65.6 | 72.3 | 78.8 | 85.1 |
| 105° | -200.7 | -183.8 | -162.4 | -138.0 | -131.6 | -125.0 | -118.3 | -111.5 | -104.7 | -97.8 | -90.9 | -83.9 | -77.0 | -70.1 | -63.2 | -56.4 |
| BYY | | | | | | | | | | | | | | | | |
| 0° | -243.2 | -254.9 | -261.7 | -263.9 | -263.8 | -263.4 | -262.7 | -261.7 | -260.4 | -258.9 | -257.1 | -254.9 | -252.5 | -249.7 | -246.6 | -243.2 |
| 15° | -160.5 | -186.3 | -208.5 | -226.9 | -231.0 | -234.7 | -238.3 | -241.5 | -244.5 | -247.3 | -249.7 | -251.8 | -253.6 | -255.1 | -256.2 | -266.9 |
| 30° | -31.0 | -64.3 | -96.1 | -125.9 | -133.0 | -140.0 | -146.8 | -153.4 | -159.8 | -166.0 | -172.0 | -177.8 | -183.6 | -188.6 | -193.5 | -198.1 |
| 45° | 110.5 | 78.3 | 45.4 | 12.1 | 3.8 | -4.4 | -12.6 | -20.8 | -28.9 | -37.0 | -44.9 | -52.7 | -60.4 | -68.0 | -75.3 | -82.5 |
| 60° | 226.2 | 203.4 | 177.9 | 150.1 | 142.9 | 135.6 | 128.1 | 120.6 | 113.0 | 105.4 | 97.7 | 89.9 | 82.2 | 74.4 | 66.7 | 59.1 |
| 75° | 285.0 | 277.4 | 266.1 | 251.2 | 246.9 | 242.5 | 237.8 | 233.0 | 228.0 | 222.8 | 217.4 | 211.9 | 206.3 | 200.5 | 194.5 | 188.5 |
| 90° | 271.2 | 280.5 | 286.2 | 288.2 | 288.0 | 287.7 | 287.1 | 286.2 | 285.2 | 283.9 | 282.3 | 280.5 | 278.6 | 276.3 | 273.9 | 271.2 |
| 105° | 188.5 | 211.9 | 233.0 | 251.2 | 255.2 | 259.1 | 262.7 | 266.1 | 269.3 | 272.2 | 274.9 | 277.4 | 279.7 | 281.7 | 283.5 | 285.0 |
| BZZ | | | | | | | | | | | | | | | | |
| 0° | 41.2 | 47.1 | 49.9 | 50.7 | 50.7 | 50.5 | 50.2 | 49.9 | 49.4 | 48.8 | 48.0 | 47.1 | 46.0 | 44.6 | 43.1 | 41.2 |
| 15° | 33.4 | 41.5 | 46.2 | 49.0 | 49.4 | 49.8 | 50.0 | 50.1 | 50.1 | 50.0 | 49.8 | 49.5 | 48.9 | 48.2 | 47.3 | 46.2 |
| 30° | 23.3 | 33.0 | 39.4 | 43.9 | 44.8 | 45.6 | 46.3 | 46.9 | 47.5 | 49.7 | 48.3 | 48.5 | 48.6 | 48.6 | 48.4 | 48.0 |
| 45° | 11.7 | 22.4 | 30.0 | 35.9 | 37.1 | 38.4 | 39.5 | 40.6 | 41.6 | 42.5 | 43.4 | 44.2 | 44.9 | 45.6 | 46.1 | 46.6 |
| 60° | -0.8 | 10.2 | 18.4 | 25.4 | 26.9 | 28.5 | 30.0 | 31.4 | 32.9 | 34.2 | 35.6 | 36.9 | 38.2 | 39.5 | 40.7 | 42.0 |
| 75° | -13.2 | -2.7 | 5.7 | 13.1 | 14.9 | 16.7 | 18.4 | 20.2 | 21.9 | 23.6 | 25.4 | 27.1 | 28.9 | 30.7 | 32.6 | 34.5 |
| 90° | -24.7 | -15.4 | -7.5 | 0.0 | 1.9 | 3.7 | 5.6 | 7.5 | 9.4 | 11.4 | 13.4 | 15.4 | 17.6 | 19.8 | 22.2 | 24.7 |
| 105° | -34.5 | -27.1 | -20.2 | -13.1 | -11.3 | -9.5 | -7.6 | -5.7 | -3.7 | -1.6 | 0.5 | 2.7 | 5.1 | 7.6 | 10.3 | 13.2 |

Sensitive Volume Dimensions

Aside from the B0 value itself, there exists a narrow spectrum of the fields' values permitting NMR signal reception at $\omega_0$ that may be represented by a Lorenzian/Gaussian lineshape, such that $$B0^- < B0 < B0^+$$

where $B_{0^-}$ and $B_{0^+}$ are some limiting magnitude field values that correspond to the probability of the NMR signal received. $B_{0^-}$ and $B_{0^+}$ define the outer and inner limiting shells of the sensitive volume, respectively.

Figure 14:
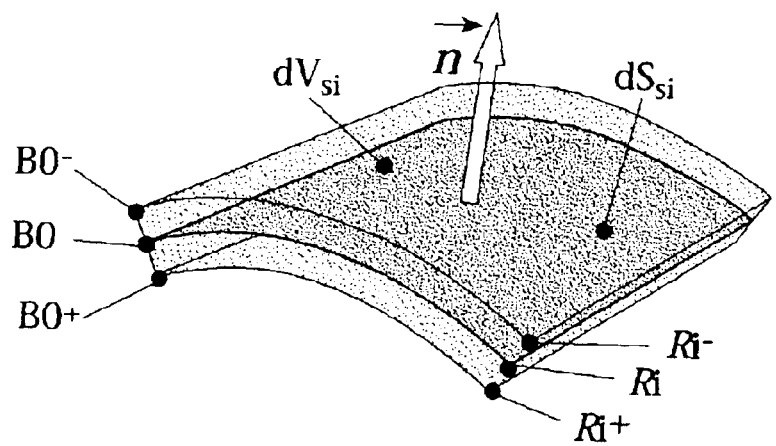
FIG. 14 shows an elementary volume of sensitive volume.

FIG. 14 shows an elementary volume of a sensitive volume. When a surface $dS_{Si}$ shrinks into the point, it is evident that a sensitive volume of i-number will be expressed by the equation $$dV_{Si} = \lim_{dS_{Si} \to 0} |dS_{Si} \cdot (\mathfrak{R}_i^- - \mathfrak{R}_i^+)|, \quad (9)$$

where $\mathfrak{R}_i^-$ and $\mathfrak{R}_i^+$ are some generalized coordinates in the normal (to area $dS_{Si}$) direction corresponding to equipotential field surfaces of $B_{0_i^-}$ and $B_{0_i^+}$.

A difference $(\mathfrak{R}_i^- - \mathfrak{R}_i^+)$ from Eq. (9) can be evaluated from the following relationship:

$$\frac{(B0_i^- - B0_i^+)}{(\mathfrak{R}_i^- - \mathfrak{R}_i^+)} = \frac{\partial B0}{\partial \mathfrak{R}_i}\bigg|_{\mathfrak{R}_i = \mathfrak{R}^{ii}}. \quad (10)$$

Since the relative estimation of the twisting effect is performed in this analysis at the same Larmor frequency, excitation level, and the sample properties, $B_{0_i^+}$ and $B_{0_i^-}$ are constant values not depending on twist angle $\tau$. Therefore, their difference $(B_{0_i^-} - B_{0_i^+})$ will also be constant for all $\tau$ values.

Furthermore, since a surface B0 is an equipotential surface (by its nature), then the direction of the normal to this surface, at any point i lying on the surface, is collinear with the B0 field gradient direction at point i. Thus, Eq. (10) can be rewritten as follows:

$$(\mathfrak{R}_i^- - \mathfrak{R}_i^+) = \frac{(B0^- - B0^+)}{\mathrm{grad}(B0)|_{\mathfrak{R}_i = \mathfrak{R}^{ii}}}. \quad (11)$$

And the entire sensitive volume can be defined as follows:

$$V_S = (B0^- - B0^+) \cdot \lim_{n \to \infty} \sum_{i=0}^{n} \frac{dS_{Si}}{\mathrm{grad}(B0)|_{\mathfrak{R}_i = \mathfrak{R}^{ii}}}. \quad (12)$$

Gradient of the B0 Field

Expressions for a B0 field gradient can be obtained easily by the one skilled in the art from equations' system Eq. (6)–(8). The general expansion of grad(Bsum) at any point in the Cartesian coordinate system (using Eqs. (6)–(8) and taking into account the expression $\mathrm{Bsum} = \sqrt{Bx^2 + By^2 + Bz^2}$) is given by:

$$\mathrm{grad}(\mathrm{Bsum}) = \frac{\sqrt{\left(B_x \frac{\partial Bx}{\partial x} + B_y \frac{\partial By}{\partial x} + B_x \frac{\partial Bz}{\partial x}\right)^2 + \left(B_x \frac{\partial Bx}{\partial y} + B_y \frac{\partial By}{\partial y} + B_z \frac{\partial Bz}{\partial y}\right)^2 + \left(B_x \frac{\partial Bx}{\partial z} + B_y \frac{\partial By}{\partial z} + B_z \frac{\partial Bz}{\partial z}\right)^2}}{\mathrm{bSum}} \quad (13)$$

Calculation of the B1 Field

Figure 15:
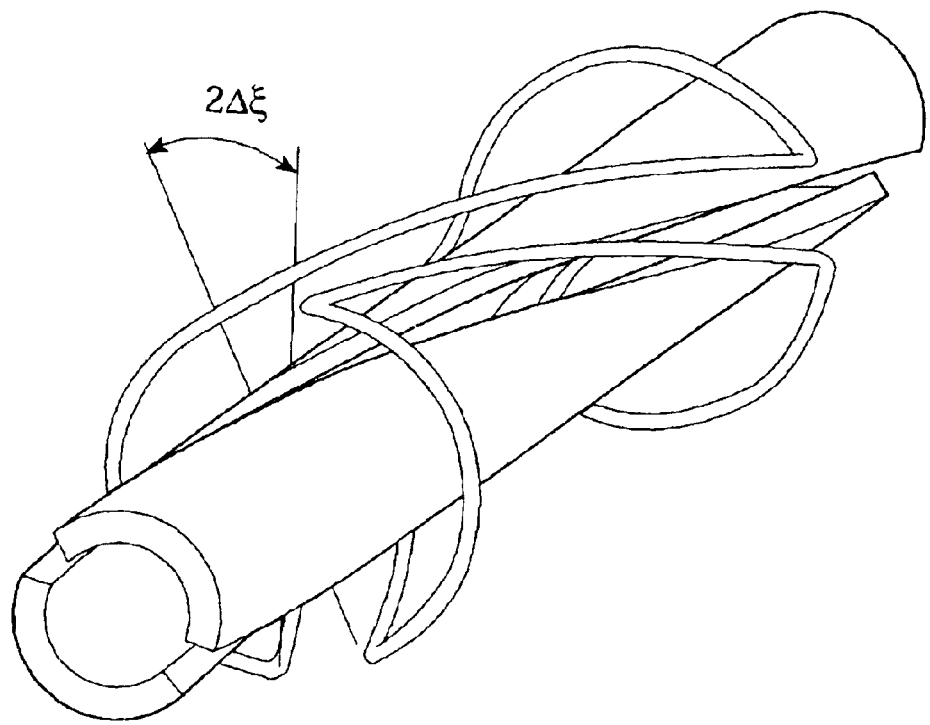
FIG. 15 shows a twisted saddle-shaped antenna paired with the twisted magnetic system.

FIG. 15 shows a twisted saddle-shaped antenna paired with the twisted magnetic system. Evaluating the B1 absolute value is not important here, since the SNR absolute value is not being sought, although it is important to accurately represent, as much as possible, the B1 field distribution in the sensitive volume zone. Thus, the constant values and time-dependent variables in the expression for B1 are not included. To obtain analytical expressions for the B1 field of such an antenna Biot-Savart's Law is used, taking into account the twist coefficient t defined in Eq. (4).

Figure 16:
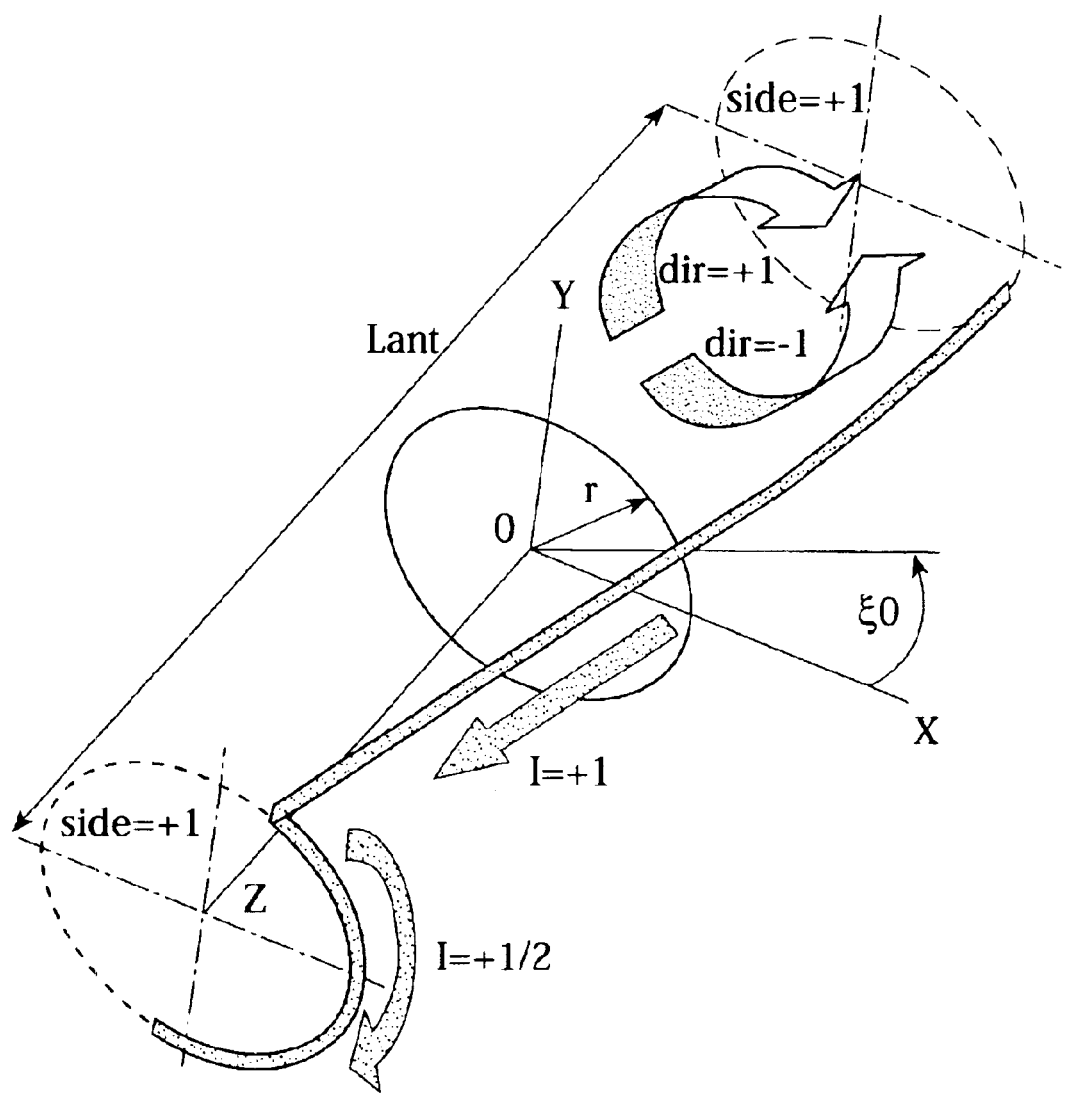
FIG. 16, shows a saddle-shaped antenna comprised of a combination of longitudinal and arc-shaped conductors.

A saddle-shaped antenna is comprised of a combination of longitudinal and arc-shaped conductors. Therefore, it will be sufficient to obtain general expressions for these two types of shapes. Accordingly, with the designations shown in FIG. 16, a magnetic field generated by longitudinal and arc-shaped conductors can be estimated at any point of space using the corresponding Eqs. (14)–(16) and Eqs. (17)–(19):

$$\mathrm{Bx\_aL}(I, \xi 0, R, \theta, Zt) := I \cdot \int_{-\frac{Lant}{2}}^{\frac{Lant}{2}} \frac{r \cdot t \cdot (Zt - z) \cdot \cos(t \cdot z + \xi 0) - (R \cdot \sin(\theta) - r \cdot \sin(t \cdot z + \xi 0))}{\sqrt{[(R \cdot \cos(\theta) - r \cdot \cos(t \cdot z + \xi 0))^2 + R \cdot \sin(\theta) - r \cdot \sin(t \cdot z + \xi 0))^2 + (Zt - z)^2]^3}} dz \quad (14)$$

$$\mathrm{By\_aL}(I, \xi 0, R, \theta, Zt) := I \cdot \int_{-\frac{Lant}{2}}^{\frac{Lant}{2}} \frac{(R \cdot \cos(\theta) - r \cdot \cos(t \cdot z + \xi 0)) + r \cdot t \cdot (Zt - z) \cdot \sin(t \cdot z + \xi 0)}{\sqrt{[(R \cdot \cos(\theta) - r \cdot \cos(t \cdot z + \xi 0))^2 + (R \cdot \sin(\theta) - r \cdot \sin(t \cdot z + \xi 0))^2 + (Zt - z)^2]^3}} dz \quad (15)$$

$$\mathrm{Bz\_aL}(I, \xi 0, R, \theta, Zt) := I \cdot \int_{-\frac{Lant}{2}}^{\frac{Lant}{2}} -r \cdot t \cdot \frac{R \cdot \cos(\theta - t \cdot z - \xi 0) - r}{\left(\sqrt{[(R \cdot \cos(\theta) - r \cdot \cos(t \cdot z + \xi 0))^2 + (R \cdot \sin(\theta) - r \cdot \sin(t \cdot z + \xi 0))^2 + (Zt - z)^2]^3}\right)} dz \quad (16)$$

-continued $$Bx\_aR(I, \xi0, R, \theta, Zt, side, dir) := \frac{I}{2} \cdot \int_{\xi 0+t \cdot \frac{Lant}{2} \cdot side}^{\xi 0+t \cdot \frac{Lant}{2} \cdot side + \pi \cdot dir} \frac{r \cdot \cos(\psi) \cdot \left(Zt - \frac{Lant}{2} \cdot side\right)}{\sqrt{\left[(R \cdot \cos(\theta) - r \cdot \cos(\psi))^2 + (R \cdot \sin(\theta) - r \cdot \sin\psi))^2 + \left(Zt - \frac{Lant}{2} \cdot side\right)^2\right]^3}} d\psi \quad (17)$$

$$By\_aR(I, \xi0, R, \theta, Zt, side, dir) := \frac{I}{2} \cdot \int_{\xi 0+t \cdot \frac{Lant}{2} \cdot side}^{\xi 0+t \cdot \frac{Lant}{2} \cdot side + \pi \cdot dir} \frac{r \cdot \sin(\psi) \cdot \left(Zt - \frac{Lant}{2} \cdot side\right)}{\sqrt{\left[(R \cdot \cos(\theta) - r \cdot \cos(\psi))^2 + (R \cdot \sin(\theta) - r \cdot \sin(\psi))^2 + \left(Zt - \frac{Lant}{2} \cdot side\right)^2\right]^3}} d\psi \quad (18)$$

$$Bz\_aR(I, \xi0, R, \theta, Zt, side, dir) := \frac{I}{2} \cdot \int_{\xi 0+t \cdot \frac{Lant}{2} \cdot side}^{\xi 0+t \cdot \frac{Lant}{2} \cdot side + \pi \cdot dir} -r \cdot \frac{R \cdot \cos(\theta - \psi) - r}{\sqrt{\left[(R \cdot \cos(\theta) - r \cdot \cos(\psi))^2 + (R \cdot \sin(\theta) - r \cdot \sin(\psi))^2 + \left(Zt - \frac{Lant}{2} \cdot side\right)^2\right]^3}} d\psi \quad (19)$$

Thus, taking into account equations (14)—(16) and (17)–(19), an antenna field comprised of two longitudinal conductors and four arc-shaped conductors can be described as follows:

$B1x(I,\xi,0R,\theta,Zt):=Bx\_aL(I,\xi0,R,\theta,Zt)+Bx\_aL(-I,\xi0+\pi,R,\theta,Zt)++$
$\quad Bx\_aR(I,\xi0,R,\theta,Zt,1,1)+Bx\_aR(I,\xi0,R,\theta,Zt,1,-1)+$ $Bx\_aR(-I,\xi0,R,\theta,Zt,-1,1)+Bx\_aR(-I,\xi0,R,\theta,Zt,-1,-1)$ (20)

$B1y(I,\xi0,R,\theta,Zt):=By\_aL(I\xi0,R,\theta,Zt)+By\_aL(-I,\xi0+\pi,R,\theta,Zt)++$
$\quad (By\_aR(I,\xi0,R,\theta,Zt,1,1)+By\_aR(I,\xi0,R,\theta,Zt,1,-1)+$ $By\_aR(-I,\xi0,R,\theta,Zt,-1,1)+By\_aR(-I,\xi0,R,\theta,Zt,-1,-1)$ (21)

$B1z(I,\xi0,R,\theta,Zt):=Bz\_aL(I,\xi0,R,\theta,Zt)+Bz\_aL(-I,\xi0+\pi,R,\theta,Zt)+$ $+(Bz\_aR(I,\xi0,R,\theta,Zt,1,1)+Bz\_aR(I,\xi0,R,\theta,Zt,1,-1)+Bz\_aR(-I,\xi0,$
$\quad R,\theta,Zt,-1,1)+Bz\_aR(-I,\xi0,R,\theta,Zt,-1,-1)$ (22)

Superposition of the two antennas having an angular displacement of $2\Delta\xi$ (of one antenna to the other) leads to the saddle-shaped geometry of the double loops antenna depicted in FIG. 15.

Comparative SNR Estimation Example

Here, as an example, one basic tool and four various twisted tools differing only by the twist angle $\tau$ ($\tau=\pi/2$, $\tau=\pi$, $\tau=3\pi/2$, $\tau=2\pi$) and by $\Delta\xi$ are used. Each one of the tools' antennas, represented by the twisted saddle-shaped antenna, has two loops. The antennas' dimensions are as follows: r=3", Lant=24", and $0° \leq \Delta\xi \leq 20°$ (see FIGS. 15, 16).

Evaluation Steps

1. Define the nodes of the sensitive area and values of $B0_x$, $B0_y$, and $B0_z$ in the nodes by using expressions (6), (7), and (8) for the constant magnetic field components (assuming B0=130 Gauss). Since the sensitive volume has an evident symmetry, it is sufficient to consider only its quarter. In the case of a rough division of the sensitive area, it is acceptable to use interpolation.
2. Define the gradient B0 using (13) for each i-node of the sensitive area.
3. Define the B1 components using (20)–(22) for each i-node of the sensitive area.
4. Define the elementary squares $dS_{si}$ of the sensitive area.
5. Optimize the expression (1) with the goal of obtaining the maximal SNR($\tau$) for each of the five cases by finding B1 (90°, $\tau$) and $\Delta\xi(\tau)$ for the optimal cases.
6. Compare the SNR($\tau$) optimization results.

Results of Analysis

Table 3 shows that during twisting (under the condition that the tool is motionless), SNR tends to increase up to $\tau=3\pi/2$. This phenomenon mainly occurs because while twisting, the B0 field gradient in the sensitive radius tends to decrease when the twist angle increases (by 5–7% in average). As a consequence, an increase in the sensitive shell thickness is observed, which corresponds to a stronger NMR signal coming from the sensitive volume. The estimated relative change in the SNR of the twisted sensor (last column in Table 3) is within a few percents only. This result allows to conclude that the twisted configuration of the NMR sensor is feasible.

TABLE 3

| $\tau$ | $\frac{B1(90°, \tau)}{B1(90°, \tau = 0)}$ | Optimal $\Delta\xi$ | $\frac{SNR(\tau)}{SNR(\tau = 0)}$ |
|---|---|---|---|
| 0 | 1 | 0° | 1 |
| $\pi/2$ | 0.999 | 0° | 1.005 |
| $\pi$ | 0.997 | 0° | 1.015 |
| $3/2\pi$ | 1.000 | 0° | 1.020 |
| $2\pi$ | 1.018 | 0° | 1.014 |

As a result of the optimization, using the "maximal SNR" criterion, the angle $2\Delta\xi$, FIG. 15, tends to 0°. In other words, the linear conductors of the antenna, where the one-directional currents are flowing, tend to coincide. The reason for this is that such a position of the antenna loops at receiving mode ensures a higher signal amplification (the main signal comes from the zones of the sensitive volume, located along the N-S direction, where the lower gradient of B0 takes place).

Without further elaboration the foregoing will so fully illustrate the invention that others may, by applying current or future knowledge, adapt the same for use under various conditions of service. Although the present invention has been described in connection with the preferred embodiments, it is not intended to be limited to these embodiments but rather is intended to cover such modifications, alternatives, and equivalents as can be reasonably included within the spirit and scope of the invention, as defined by the following claims.

What is claimed is:

1. An apparatus for making nuclear magnetic resonance (NMR) measurements, comprising:
   a. a magnet having a longitudinal axis, the magnet being twisted about the longitudinal axis to form a helical spatial configuration and to generate a helical static magnetic field substantially perpendicular to the longitudinal axis;
   b. an antenna configured to generate a radio frequency (RF) magnetic field substantially perpendicular to the static magnetic field of the magnet and to receive NMR signals from excited nuclei; and c. a protective collar overlaying at least a portion of the magnet and having a helical configuration substantially similar to the spatial configuration of the magnet.

2. The apparatus of claim 1, wherein the protective collar has one or more lateral projections extending outward from the collar and having substantially similar helical spatial configuration.

3. The apparatus of claim 2, wherein the lateral projections comprise two lateral projections on opposite sides of the protective collar.

4. The apparatus of claim 3, wherein the protective collar has a twist angle that produces a 180° turn over the length of the magnet.

5. The apparatus of claim 1 further comprising drilling means.

6. The apparatus of claim 5, wherein the drilling means comprises a drill bit mounted on the protective collar.

7. The apparatus of claim 1, wherein the antenna is mounted in a recess of the protective collar.

8. The apparatus of claim 7, wherein the antenna is electrically isolated from the protective collar.

9. The apparatus of claim 7, wherein the antenna produces an approximation of a magnetic dipole field.

10. The apparatus of claim 7, wherein the antenna comprises two pairs of elongated conductors disposed along the length of the protective collar.

11. The apparatus of claim 10, wherein each of said conductors is of a relatively narrow width defined by an arc of a first predetermined polar angle measured with respect to said axis, and wherein the distance between the centers of the arcs of each pair of conductors is a second predetermined polar angle measured with respect to said axis.

12. The apparatus of claim 11, wherein said first predetermined polar angle is approximately 15°.

13. The apparatus of claim 11, wherein said second predetermined polar angle is approximately 20°.

14. The apparatus of claim 10, wherein said pairs of electrical conductors are connected in series with each other, and wherein conductors of each pair are connected in parallel with each other.

15. The apparatus of claim 7, wherein the antenna has a twisted saddle-shape.

16. The apparatus of claim 7, wherein the antenna comprises a combination of longitudinal and arc-shaped conductors.

17. The apparatus of claim 1, wherein the protective collar is made of non-magnetic metal or metal alloy and the apparatus further comprises an electrically insulating and non-magnetic sleeve enclosing the collar and the antenna.

18. The apparatus of claim 17, wherein the sleeve comprises fiberglass.

19. The apparatus of claim 1, wherein the protective collar is made of non-magnetic metal alloy, including one or more of: Inconel 718, Monel metal and P-550 alloy.

20. The apparatus of claim 1, wherein said static magnetic field of the magnet is a gradient static magnetic field.

21. The apparatus of claim 1, wherein the magnet comprises a plurality of segments, successive segments being offset, so as to form an overall helical configuration over the length of the magnet.

22. The apparatus of claim 1, wherein the helical spatial configuration of the magnet comprises two or more sections, in which the angle or twist about the axis are different.

23. The apparatus of claim 1, wherein the angle of twist over the length of the magnet is 180°.

24. A method for manufacturing NMR measurement devices, comprising the steps of:

a. providing a magnet having a longitudinal axis, the magnet being twisted about the longitudinal axis to form a helical spatial configuration and to generate a helical static magnetic field substantially perpendicular to the longitudinal axis;

b. installing a protective collar overlaying at least a portion of the magnet and having a helical configuration substantially similar to the spatial configuration of the magnet; and c. mounting in a recess of the protective collar an antenna configured to generate a radio frequency (RF) magnetic field substantially perpendicular to the static magnetic field of the magnet and to receive NMR signals from excited nuclei.

25. The method of claim 24, wherein the step of installing a protective collar comprises installing one or more lateral projections extending outward from the collar and having substantially similar helical spatial configuration.

26. The method of claim 24 further comprising the step of installing drilling means comprising a drill bit mounted on the protective collar.

27. The method of claim 24, wherein step of mounting the antenna comprises the step of providing an electrical isolation from the protective collar.

28. The method of claim 24 further comprising the step of installing an electrically insulating and non-magnetic sleeve enclosing the collar and the antenna.

29. The method of claim 24, wherein the step of providing a magnet comprises providing a plurality of segments, successive segments being offset, so as to form an overall helical configuration over the length of the magnet.

* * * * *